United States Patent
Kammer et al.

(10) Patent No.: US 11,819,451 B2
(45) Date of Patent: Nov. 21, 2023

(54) INJECTABLE SLUSH FEED SUPPLY

(71) Applicant: C° Change Surgical LLC, Winston-Salem, NC (US)

(72) Inventors: Patrick Kammer, Greensboro, NC (US); Kevin Joseph Rackers, Summerfield, NC (US); Philip Morrison Allred, III, Kernersville, NC (US)

(73) Assignee: C° Change Surgical LLC, Winston-Salem, NC (US)

( * ) Notice: Subject to any disclaimer, the term of this patent is extended or adjusted under 35 U.S.C. 154(b) by 0 days.

(21) Appl. No.: 18/094,886

(22) Filed: Jan. 9, 2023

(65) Prior Publication Data

US 2023/0149210 A1 May 18, 2023

Related U.S. Application Data

(63) Continuation of application No. PCT/US2021/041269, filed on Jul. 12, 2021.
(Continued)

(51) Int. Cl.
*A61F 7/12* (2006.01)
*A61F 7/00* (2006.01)

(52) U.S. Cl.
CPC .............. *A61F 7/12* (2013.01); *A61F 7/0085* (2013.01); *A61F 2007/0063* (2013.01); *A61F 2007/126* (2013.01)

(58) Field of Classification Search
CPC ....................... A61F 7/0085; A61F 7/00; A61F 2007/0063; A61F 7/12; A61F 2007/126;
(Continued)

(56) References Cited

U.S. PATENT DOCUMENTS

| 5,507,790 A | 4/1996 | Weiss |
| 6,620,188 B1 | 9/2003 | Ginsburg |

(Continued)

FOREIGN PATENT DOCUMENTS

| EP | 3586804 A1 | 1/2020 |
| KR | 200348008 Y1 | 4/2004 |

(Continued)

OTHER PUBLICATIONS

Jun, Sun Ae, PCT International Preliminary Report on Patentability for International Application No. PCT/US2021/041269, dated Nov. 2, 2022, 6 pages, Korean Intellectual Property Office, Daejeon, South Korea.

*Primary Examiner* — Joseph A Stoklosa
*Assistant Examiner* — Adam J Avigan
(74) *Attorney, Agent, or Firm* — Kevin E Flynn; FLYNN IP LAW

(57) ABSTRACT

A process and related assemblies for delivering slush through a tube towards a patient. Obtaining an elongated container partially filled with slush with a port end that has a first port and a second port. Placing the first port in fluid communication with tubing for delivery of slush towards the patient. Placing the second port in fluid communication with a source of gas which may be air. Subjecting the elongated container to automated repetitive movements so that the slush in the partially filled elongated container moves against interior surfaces within the elongated container. Ideally, two different forms of repetitive motion are used to impose complex movement upon the slush within the elongated container. Applying a pressure gradient to cause slush to flow out of the first port towards the patient. The elongated container may be made from a slush bottle with a reversibly engaged cap with the two ports.

35 Claims, 11 Drawing Sheets

Related U.S. Application Data

(60) Provisional application No. 63/050,515, filed on Jul. 10, 2020.

(58) Field of Classification Search
CPC ....... A61F 2007/0059; F25C 2301/002; A61B 2050/0014
See application file for complete search history.

(56) References Cited

U.S. PATENT DOCUMENTS

| | | | |
|---|---|---|---|
| 7,122,021 B2 | 10/2006 | Ahlstrom | |
| 7,367,341 B2 | 5/2008 | Anderson | |
| 7,588,547 B2 | 9/2009 | Deem | |
| 8,100,880 B2 | 1/2012 | Burnett | |
| 8,439,960 B2 | 5/2013 | Burnett | |
| 8,475,441 B2 | 7/2013 | Babkin | |
| 8,672,884 B2 | 3/2014 | Burnett | |
| 8,676,338 B2 | 3/2014 | Levinson | |
| 8,784,385 B2 | 7/2014 | Boyden | |
| 9,132,031 B2 | 9/2015 | Levinson | |
| 9,308,120 B2 | 4/2016 | Anderson | |
| 9,314,368 B2 | 4/2016 | Allison | |
| 9,538,745 B2 | 1/2017 | He | |
| 9,549,843 B2 | 1/2017 | Kammer | |
| 9,980,765 B2 | 5/2018 | Avram | |
| 10,080,759 B2 | 9/2018 | Ji | |
| 10,286,030 B2 | 5/2019 | Garruto | |
| 10,493,011 B2 | 12/2019 | Widgerow | |
| 10,500,342 B2 | 12/2019 | Velis | |
| 10,582,960 B2 | 3/2020 | Avram | |
| 10,688,147 B2 | 6/2020 | Garruto | |
| 11,000,409 B2 | 5/2021 | Velis | |
| 11,197,776 B2 | 12/2021 | Anderson | |
| 11,439,532 B2 | 9/2022 | Velis | |
| 11,446,178 B2 | 9/2022 | Velis | |
| 11,504,322 B2 | 11/2022 | Garibyan | |
| 2003/0074038 A1* | 4/2003 | Gruszecki | A61F 7/0085 607/104 |
| 2004/0073175 A1* | 4/2004 | Jacobson | A61M 5/14244 604/251 |
| 2006/0025755 A1 | 2/2006 | Landman | |
| 2006/0036302 A1 | 2/2006 | Kasza | |
| 2006/0161232 A1 | 7/2006 | Kasza | |
| 2007/0010861 A1 | 1/2007 | Anderson | |
| 2007/0106247 A1 | 5/2007 | Burnett | |
| 2007/0255362 A1 | 11/2007 | Levinson | |
| 2007/0265608 A1 | 11/2007 | Hernandez | |
| 2009/0118722 A1 | 5/2009 | Ebbers | |
| 2009/0218704 A1 | 9/2009 | Murakami | |
| 2009/0326621 A1* | 12/2009 | El-Galley | A61F 7/12 607/105 |
| 2010/0204765 A1 | 8/2010 | Hall | |
| 2013/0190744 A1 | 7/2013 | Avram | |
| 2015/0119962 A1* | 4/2015 | Kulstad | A61F 7/0085 607/105 |
| 2015/0230976 A1 | 8/2015 | Rogers | |
| 2016/0151200 A1 | 6/2016 | Kammer | |
| 2016/0175141 A1 | 6/2016 | Wu | |
| 2017/0274011 A1 | 9/2017 | Garibyan | |
| 2017/0274078 A1 | 9/2017 | Garibyan | |
| 2018/0094232 A1 | 4/2018 | Toner | |
| 2018/0116868 A1 | 5/2018 | Velis | |
| 2018/0214300 A1 | 8/2018 | Anderson | |
| 2018/0250056 A1 | 9/2018 | Avram | |
| 2018/0289537 A1 | 10/2018 | Velis | |
| 2018/0289538 A1 | 10/2018 | Velis | |
| 2019/0029876 A1 | 1/2019 | Anderson | |
| 2019/0192424 A1 | 6/2019 | Garibyan | |
| 2020/0046552 A1 | 2/2020 | Velis | |
| 2021/0030457 A1 | 2/2021 | Avram | |
| 2021/0244817 A1 | 8/2021 | Garibyan | |
| 2022/0079448 A1 | 3/2022 | Nadkarni | |
| 2022/0079874 A1 | 3/2022 | Garibyan | |

FOREIGN PATENT DOCUMENTS

| | | |
|---|---|---|
| KR | 20150013792 A | 2/2015 |
| KR | 20180122642 A | 11/2018 |
| WO | 2016033380 A1 | 3/2016 |
| WO | 2020/077089 A1 | 4/2020 |

\* cited by examiner

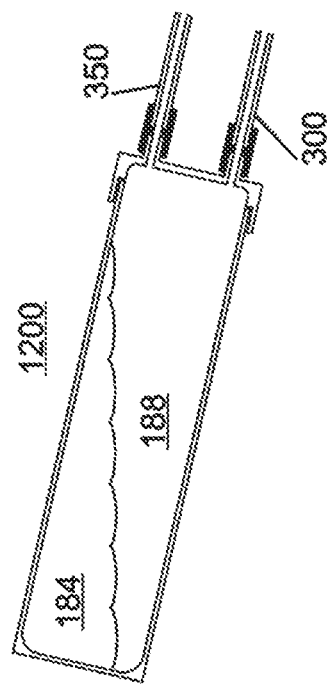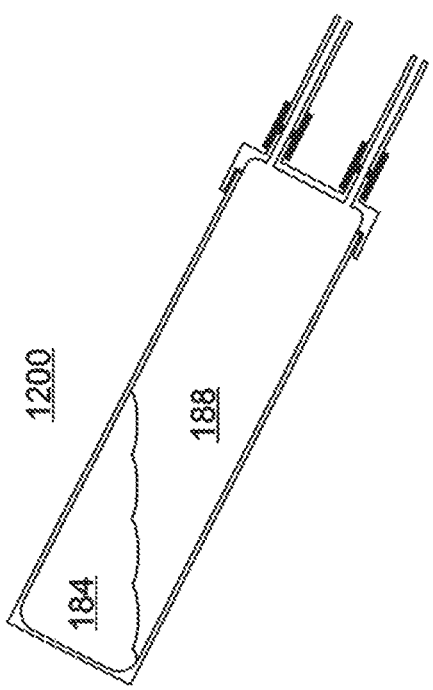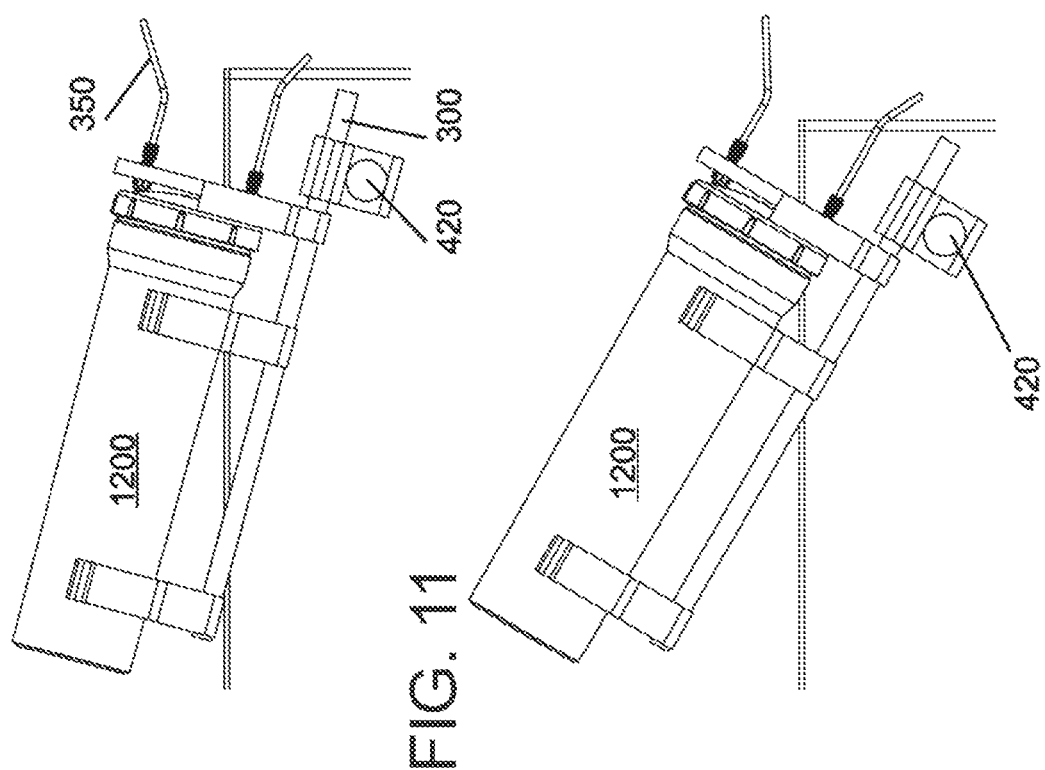

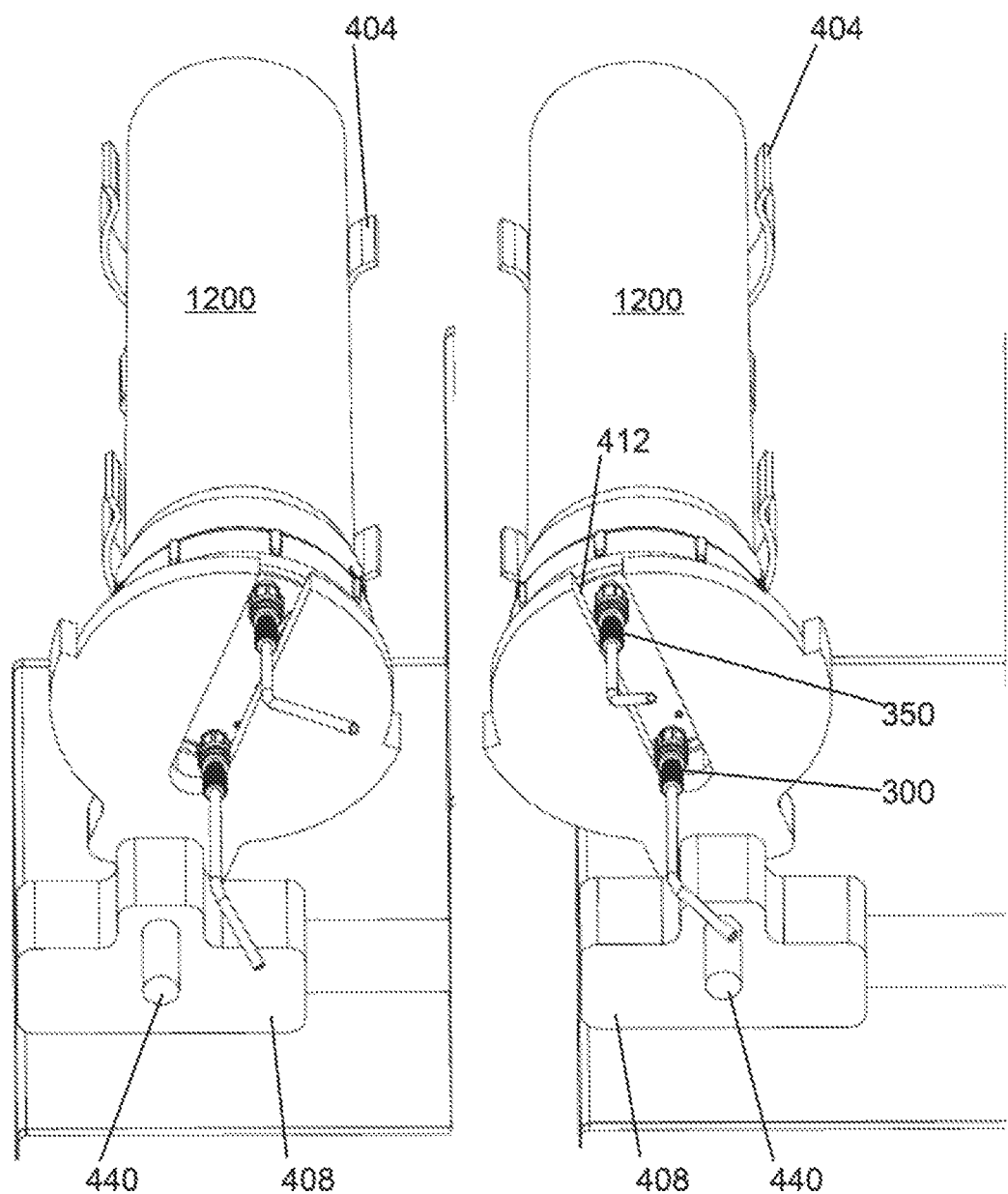

INJECTABLE SLUSH FEED SUPPLY

This disclosure claims the priority benefit of commonly assigned, and co-pending Patent Cooperation Treaty Application PCT/US2021/041269 filed Jul. 12, 2021 with title Injectable Slush Feed Supply. The '269 application claims the benefit of U.S. Provisional Patent Application No. 63/050,515 filed Jul. 10, 2020 with title Injectable Slush Feed Supply. The '515 and the '269 applications are incorporated by reference herein.

BACKGROUND

Field of the Disclosure

This disclosure relates generally to the controlled delivery of a sterile therapeutic medium such as sterile surgical slush for use in surgery or other therapeutic uses. The patients receiving the therapy may be human or non-human animals.

Related Art

Production of Sterile Slush.

Sterile saline slush has long been used in a variety of surgical applications to slow organ and tissue metabolic rates thereby protecting organs from irreversible tissue damage during cardiac, neurological organ transplant, vascular, urologic and other complex surgeries. For these uses, it is important that the slush has as smooth and spherical a configuration as possible to ensure atraumatic slush without sharp crystal edges that could puncture or damage tissue. The slush should have a substantially uniform consistency to maintain optimal thermodynamic cooling performance. Surgical slush is a mix of ice crystals formed while cooling saline and some amount of liquid saline that remains in liquid form.

Desirable surgical slush has a substantially uniform consistency. Desirable surgical slush will feel soft to the touch without any hard, crystalline formations. Thus, the ice crystals created for use in a snow cone would not be acceptable and that sort of consistency is to be avoided through controlling the slush creation process.

U.S. Pat. No. 9,549,843 for the Production of Well-Mixed Surgical Slush addresses processes of creation of surgical slush from a base of sterile saline which may have additional therapeutic agents. The contents of the '843 patent are incorporated by reference herein in their entirety.

Ideally, the sterile surgical slush is made in a controlled manner so that the slush slurry has desirable mechanical properties so that the sterile surgical slush can be introduced into a surgical site without causing mechanical trauma to the tissue. The '843 patent teaches ways of keeping the contents of the slush container agitated and mixed so that the slush is distributed substantially evenly throughout the slush container and avoids the creation of large slush ice structures. Atraumatic slush that is desirable for use in surgical procedures may be produced with this process.

More Detailed Examination of Slush Formation.

As energy is removed from a liquid, the temperature continues to fall until the temperature reaches the point at which crystal formation begins. Crystallization can be broken down into two parts, nucleation and crystal growth. Nucleation occurs when molecules start to arrange into a defined crystal structure. Crystal growth occurs on the nucleus crystal formed during nucleation.

During nucleation, an interface is formed at the boundary between the solid and liquid phases of water. Creation of this boundary is actually an exothermic process which means that heat and pressure are released. In order for a stable nucleus to form, the fluid temperature must be sufficiently below the melting point of the fluid (super cooled) to absorb the energy release during nucleation without causing the temperature to rise above the melting point. The amount of super cooling needed to initiate nucleation depends on whether or not there are nucleators in the fluid.

Nucleators are things like impurities, undissolved solids, and irregularities on the container walls. Without nucleators, the fluid goes through homogeneous nucleation and requires significant super cooling because of the large amount of energy required to form a crystalline surface boundary where no boundary previously existed. When nucleators are present the fluid goes through heterogeneous nucleation and a stable nucleus can be formed at the site of the nucleator with temperatures just slightly below the melting point.

The crystal growth part of freezing is also an exothermic process. As long as the heat produced by crystal growth is removed, the freezing process will continue. If the fluid is sufficiently super cooled before any nucleation occurs, the initial crystal growth can be very fast. For instance, a water bottle that is super cooled to −20 degrees Celsius before nucleation can have about 25% of the fluid turn to ice in about two or three seconds when something happens to initiate freezing. The trigger to initiate freezing may be the addition of an impurity. Another possible trigger to initiate freezing is bumping the bottle on a table such that a pressure wave propagates through the liquid.

Only 25% of the fluid will go through the phase change because the latent heat of freezing is about 80 cal/gm and the specific heat of water is about 1 calorie per degree Celsius per gram. This means the freezing process produces enough heat to raise the temperature of one gram of water by 80 Celsius, but since the water was only 20 degrees Celsius below the melting point the freezing could only occur in 20/80=25% of the fluid. In this example the liquid temperature quickly rises from −20 degrees Celsius to 0 degrees Celsius. After this initial freezing the crystal growth continues more slowly and is limited by how fast heat can be removed from the water.

If pure water is sufficiently mixed during the phase change process, the temperature of the pure water will remain at the melting point. As heat is removed which tends to reduce the temperature below the melting point, energy is available for the crystals to grow, but the crystals can only grow until the heat generated by their growth brings the temperature back up to the melting point. This balancing act between heat removal and crystal growth continues until all the liquid is frozen at which point the temperature of the ice starts to drop. If temperature variations occur within the fluid, then localized areas of freezing can occur that produce hard ice while other parts of the fluid are still completely liquid. This occurs most often at the walls of a container where heat is being removed or at the surface of a body of water like a pond that is exposed to sub-freezing temperatures.

Sterile saline slush may be made from a fluid solution that includes sodium chloride (NaCl) in water which is typically 0.9% sodium chloride by weight. The sodium chloride helps suppress the initial freezing point of the fluid to about −3.3 degrees Celsius. However, since the sodium chloride molecule is not integrated into a water crystalline structure, the concentration of sodium chloride in liquid water goes up as the percentage of water ice goes up. This increasing concentration of sodium chloride that is pushed ahead of the advancing ice causes a further reduction in the freezing point of the remaining fluid. As long as the sodium chloride molecules stay mobile and do not get trapped by a surrounding water crystal structure, the sodium chloride concentration in the remaining liquid can continue to increase and thus decrease the freezing point until about −21.1 degrees Celsius which is the temperature at which salt begins to crystallize out of solution.

Slush is essentially a collection of ice crystals surrounded by liquid. The microscopic structure and size of the ice crystals have a large impact on the macroscopic feel and appearance of the slush. A soft slush is made up of many small crystals while a slush with fewer but larger crystals will appear more granular and will have small shards of ice. Keeping the increasing sodium chloride concentration homogenous throughout the container while controlled crystal growth is occurring tends to promote the formation of many small ice crystals rather than fewer large ice crystals. Keeping the temperature of the solution homogenous is also important. Failure to maintain substantially homogenous temperature distribution leads to localized cool spots which may lead to bridges between clumps of crystals that are not easily broken as the bridges may grow extensively as the localized cool spot allows for relatively rapid freezing.

One of the most difficult areas to prevent large crystalline formation is at the container wall. Heat transfer occurs at the surface so any ice crystal that contacts the wall immediately has access to the cooling needed for rapid growth because the wall temperature will be well below the freezing point. If, however, the contact between the ice crystal and wall is brief, the quickly grown extension to the crystalline lattice is weak and can be broken when brought back into the warmer bulk fluid. The problem with rapid crystal formation at the wall is compounded as a crystal requires less energy to form a new surface between the liquid and solid phase if the crystal forms on an already existing surface.

This heterogeneous nucleation at the wall can also be accelerated if there are pits or cracks in the surface of the wall. Ice crystals form faster if the contact angle between the wall and a fluid droplet is decreased in that there is more contact with the chilled wall.

Appropriate choices for container geometry and complex mixing motion promote proper slush formation that reduces crystal contact time with the container wall and maintains a homogeneous sodium chloride concentration and temperature throughout the container. Establishing the desired mixing while the saline is still a liquid is relatively easy as the mobility of the fluid allows for easy transfer throughout a container. However, once a portion of the saline turns to slush, proper mixing becomes progressively more difficult because the slush viscosity is constantly changing as the crystal concentration increases.

The '843 Patent.

The '843 patent teaches ways of making atraumatic slush. FIG. 1 shows a side view of prior art slush container 100 with slush bottle 110 with cap 104. Mechanical agitation as the slush is being created allows small crystal formations to be formed at the nucleation sites, but size growth of the crystal formations is inhibited because mechanical agitation prevents larger crystal growth. When these small crystals are suspended in the bulk fluid, they form a slurry or slush. Mechanical agitation also helps keep the bulk fluid temperature more consistent and helps reduce large crystal growth that would otherwise occur at the fluid boundary (such as the fluid/air boundary or at any of the container walls) where heat is typically being transferred out of the fluid.

Moving the carriage to impart a sequence of accelerations to the contents of the slush container to cause the contents to move relative to the walls and lid of the container. This complex movement (something other than staying still or pure uniform rotation about the longitudinal centerline of the container) helps keep slush well mixed within the closed slush container. The slush container may be oriented with the longitudinal centerline close to horizontal so that movements of the top of the container relative to the bottom of the container promote movement of the air gap in the container from the one end of the container to the other end of the container to help keep slush from adhering to the interior walls of the container. Applying a cycle of agitation that rotates the slush container so that the start position of the container from one cycle of agitation to the next cycle of agitation exposes different portions of the slush container interior to the air gap as movement into and out of the air gap helps remove ice crystals from the interior walls.

Keeping the contents of the slush container agitated and mixed so that the slush is distributed substantially evenly throughout the slush container avoids the creation of large slush ice structures. Atraumatic slush that is desirable for use in surgical procedures may be produced with this process.

The complex movement of the slush saline mixture at the air gap may be produced by a range of different types of stimuli. Examples provided within this disclosure include asymmetric rotation reversals around a longitudinal axis if rotation proceeds for less than one full rotation before a reversal for less than one full rotation. Another type of stimulus provides for rotation around a longitudinal axis of the slush container for many revolutions without changing direction. Stimulus includes periodically dropping one or both ends of the slush container and lifting the slush container. The lifting and dropping may be implemented with humps or troughs on a rotating carriage that contains the slush container. Other forms of stimulus to lift and drop one or both ends of the slush container are disclosed.

Commercial equipment that uses the teachings of the '843 have been widely accepted for use within hospitals for the creation of atraumatic slush.

Cryotherapy or Cryolipolysis

Cryotherapy is the application of low temperature in medical therapy. Cryotherapy may be used to destroy abnormal or diseased tissue. A common use is to treat skin conditions such as the destruction of a wart.

Cryolipolysis is not directed to abnormal or diseased tissue. Cryolipolysis is the use of low temperatures to cause cell death of fat tissue ("apoptosis"). Fat tissue is more easily damaged by cooling than some other tissue types (such as skin).

An early form of cryolipolysis was achieved transdermally. This process is sometimes provided under the trademark Cool Sculpting®.

Cryolipolysis through transdermal injections of cooled material directly into the targeted fat tissue is being explored. See for example, US Patent Publication No. 2017/0274011 for Injectable Slurries and Methods of Manufacturing and Using the Same. (The '011 publication is incorporated by reference in its entirety.)

The process of making and delivering surgical slush to target tissue for cryolipolysis is in the early stages and there is room for improvements to the process of maintaining surgical slush in a useable format and in providing slush for controlled transdermal delivery.

Vocabulary.

Units.

Note that in order to provide focus on specific functions, the description below will reference various "units". In this context, a unit implies the required resources to perform a given set of functions. This may include a combination of electro-mechanical devices such as a microphone or a camera and the processing power to control the devices then manipulate the data obtained by the devices. In some instances, the functionality from several individually discussed units may be performed using physical components that are shared by several of the units discussed below.

Or.

Unless explicit to the contrary, the word "or" should be interpreted as an inclusive or rather than an exclusive or. Thus, the default meaning of or should be the same as the more awkward and/or.

Set.

Unless explicit to the contrary, the word "set" should be interpreted as a group of one or more items.

Gne and Gnes.

To avoid the awkward uses of he/she and his/her or the potentially confusing singular use of they and their, this application uses the gender-neutral pronoun gne and the possessive gnes.

Substantially.

Frequently, when describing an industrial process, it is useful to note that a given parameter is substantially met. Examples may be substantially parallel, substantially perpendicular, substantially uniform, and substantially flat. In this context, substantially X means that for purposes of this industrial process it is X. For example, something that may not be absolutely parallel but is for all practical purposes parallel, is substantially parallel. Likewise, mixed air that has substantially uniform temperature would have temperature deviations that were inconsequential for that industrial process.

As recognized in C. E. Equipment Co. v. United States, 13 U.S.P.Q.2d 1363, 1368 (Cl. Ct. 1989), the word "substantially" in patent claims gives rise to some definitional leeway—thus the word "substantially" may prevent avoidance of infringement by minor changes that do not affect the results sought to be accomplished.

Proximal and Distal.

For items that can be oriented in different directions, it is useful to have reference points of proximal and distal. For purposes of this application, the proximal end of the slush feed container 1200, the proximal end of slush output connector 300 is proximal tip 904 which would be the location to other components in the slush delivery system. Likewise, the proximal end of the vent tube 350 would be proximal tip 954 which may connect to other components in the slush delivery system or merely be open to ambient air. The distal end 920 of the slush feed container 1200 is the closed bottom of the slush bottle 240. With this set of extremes, the proximal and distal sides of components between the proximal tips (904 and 954) and the distal end 920 are clear.

Numbers are Minimums.

Numbers of items set forth in a disclosure and the claims that follow should be interpreted as minimum numbers for the relevant items unless the specificity of a number precluding more is made explicit. Thus the phrase "two ports" indicates two or more ports and the phrase "one pump" indicates one or more pumps.

Matter.

Channels through the ports and other passageways are adapted to allow for the passage of matter. Matter includes gases, liquids, and solids. Non-limiting examples of matter includes gases including air, slush, solids such as ice crystals, and liquids such as liquid saline.

Walls around a Circle.

A cylinder has a perimeter. Some may think of a wall around a circular perimeter as one wall. Some may think of a walled perimeter around a circle as a series approaching infinity of short walls that combine together to encircle a circle. This application and the claims that follow allow the expression of walls to include the structure that encircles a circular perimeter.

SUMMARY OF THE DISCLOSURE

Aspects of the teachings contained within this disclosure are addressed in the claims submitted with this application upon filing. Rather than adding redundant restatements of the contents of the claims, these claims should be considered incorporated by reference into this summary.

This summary is meant to provide an introduction to the concepts that are disclosed within the specification without being an exhaustive list of the many teachings and variations upon those teachings that are provided in the extended discussion within this disclosure. Thus, the contents of this summary should not be used to limit the scope of the claims that follow.

Inventive concepts are illustrated in a series of examples, some examples showing more than one inventive concept. Individual inventive concepts can be implemented without implementing all details provided in a particular example. It is not necessary to provide examples of every possible combination of the inventive concepts provide below as one of skill in the art will recognize that inventive concepts illustrated in various examples can be combined together in order to address a specific application.

Aspects of the teachings of the present disclosure may be summarized as an assembly for use to provide slush for injection into a patient, the assembly comprising:
   a slush bottle with an interior defined by a bottle bottom at a distal end of the slush bottle, a set of at least one bottle sidewall connecting the bottle bottom to an open end of the slush bottle at a proximal end of the slush bottle;
   a cap adapted to reversibly engage with the proximal end of the slush bottle to cover the open end and form a capped bottle;
   a set of two ports that each provide one open channel from a proximal side of the cap to a distal side of the cap to allow matter to traverse through the cap while the cap is engaged with the proximal end of the slush bottle.

Additional aspects of the teachings of the present disclosure may be summarized as adding to the assembly:
   a slush output connector connected an output port which is one of the set of two ports, the slush output connector having a delivery channel for delivery of slush from the interior of the capped bottle through the one of the set of two ports and the slush output connector to tubing that carries slush towards an entry point in the patient; and
   a vent tube connected to a vent port which is one of the set of two ports but not a port connected to the slush output connector, the vent tube having a vent channel that allows gas to flow through the vent tube and the vent port to allow gas to enter the capped bottle.

Additional aspects of the teachings of the present disclosure may be summarized as adding to the assembly a slush mixing device that supports the capped bottle and tilts the capped bottle so that a longitudinal centerline of the capped bottle from bottle bottom to cap has a movement towards horizontal followed by movement to a second position with the cap of the capped bottle lower than the bottle bottom of the capped bottle so that a water line between the slush and a gas filled space moves within the capped bottle. The slush mixing device may impose a second form of oscillation of the capped bottle to impose complex movement of the slush within the capped bottle. The second form of oscillation may be rocking the capped bottle clockwise and counterclockwise around a rocking axis running parallel to the longitudinal centerline so that rocking of the capped bottle augments the tilting of the capped bottle to agitate the slush contained in the capped bottle. The slush mixing device may rock the capped bottle using a rocking cycle of a first duration and the slush mixing device may tilt the capped bottle using a tilt cycle of a second duration that is different from the first duration.

The two forms of oscillation may be applied without stop until the capped slush bottle is no longer needed to provide slush or is no longer able to provide slush.

Alternatively, aspects of the teachings of the present disclosure may be summarized as a process for delivering slush through a tube towards a patient, the process comprising:

obtaining an elongated container which may be a capped slush bottle partially filled with slush and with a port end that has a first port and a second port;

placing the first port in fluid communication with tubing for delivery of slush towards the patient;

placing the second port in fluid communication with a source of gas;

subjecting the elongated container to two automated forms of repetitive movements so that the slush in the partially filled slush bottle moves against interior surfaces within the elongated container; and creating a pressure gradient to cause slush to flow out of the first port towards the patient.

The port end may have a slush output connector associated with the first port, to create a flow path for slush from the interior of the elongated container, through the first port and through the slush output connector. The slush output connector may be a separate piece that is connected to the first port or integrated with the first port as part of the port end.

The port end may have a vent tube associated with the second port, to create a vent path for gas from the exterior of the elongated container, through the vent tube and through the second port to the interior of the elongated container. The vent tube may be a separate part connected to the second port or may be integrated with the second port as part of the port end of the elongated container.

The port end of the elongated container with the two ports may have been the cap used while the slush bottle was in the slush making machine or it may be a cap for delivery added to the slush bottle after the creation of the slush.

Slush may be forced out of the elongated container through the use of pressurized gas applied to the vent tube associated with the second port or pump suction applied to the slush output connector associated with the first port, or a combination of both forms of force.

Efforts may be made to slow the melting of slush within the elongated container. The efforts may include chilling ambient air around the elongated container, insulating the elongated container from ambient air, or using cooling plates to absorb heat from the exterior of the elongated container.

Aspects of the teachings of the present disclosure may be summarized as an assembly for use in providing slush for injection into a patient. The assembly having:

an elongated container with an interior defined by a container bottom at a distal end of the elongated container, a port end of the elongated container opposite the container bottom, and a set of at least one container sidewall connecting the container bottom to a port end at a proximal end of the elongated container;

a set of two ports that each provide one open channel from a proximal side of the port end of the elongated container to a distal side of the port end of the elongated container to allow matter to traverse through the port end of the elongated container;

a slush output connector connected an output port which is one of the set of two ports, the slush output connector having a delivery channel for delivery of slush from the interior of the elongated container through the one of the set of two ports and the slush output connector to tubing that carries slush towards an entry point in the patient; and a vent tube connected to a vent port which is one of the set of two ports but not a port connected to the slush output connector, the vent tube having a vent channel that allows gas to flow through the vent tube and the vent port to allow gas to enter the elongated container;

a slush mixing device that supports the elongated container and tilts the elongated container so that a longitudinal centerline of the elongated container from container bottom to the port end of the elongated container has a movement towards horizontal followed by movement to a second position with the port end of the elongated container lower than the container bottom of the elongated container so that a water line between the slush and a gas filled space moves within the elongated container.

One of skill in the art will recognize that some of the alternative implementations set forth above are not universally mutually exclusive and that in some cases additional implementations can be created that employ aspects of two or more of the variations described above. Likewise, the present disclosure is not limited to the specific examples or particular embodiments provided to promote understanding of the various teachings of the present disclosure. Moreover, the scope of the claims which follow covers the range of variations, modifications, and substitutes for the components described herein as would be known to those of skill in the art.

Other systems, methods, features and advantages of the disclosed teachings will be immediately apparent or will become apparent to one with skill in the art upon examination of the following figures and detailed description. It is intended that all such additional systems, methods, features and advantages be included within the scope of and be protected by the accompanying claims.

BRIEF DESCRIPTION OF THE FIGURES

The disclosure can be better understood with reference to the following figures. The components in the figures are not necessarily to scale, emphasis instead being placed upon illustrating the principles of the disclosure. Moreover, in the figures, like reference numerals designate corresponding parts throughout the different views.

FIG. 9 shows a slush feed container 1200 and a portion of a slush mixing device 400.

FIG. 10 shows a simplified cross section of the slush feed container 1200 at a 15 degrees downward tilt.

FIG. 11 shows a slush feed container 1200 and a portion of a slush mixing device 400.

FIG. 12 shows a simplified cross section of the slush feed container 1200 at a 30 degrees downward tilt.

FIG. 15 and FIG. 16 show a slush mixing device 400 that has active rocking imposed by rocking shaft 440 upon the cradled slush feed container 1200.

DETAILED DESCRIPTION

The presently disclosed subject matter is described with specificity to meet statutory requirements. However, the description itself is not intended to limit the scope of this patent. Rather, the inventors have contemplated that the claimed subject matter might also be embodied in other ways, to include different steps or elements similar to the ones described in this document, in conjunction with other present or future technologies. Moreover, although the term "step" may be used herein to connote different aspects of methods employed, the term should not be interpreted as implying any particular order among or between various steps herein disclosed unless and except when the order of individual steps is explicitly described.

Figure 1:
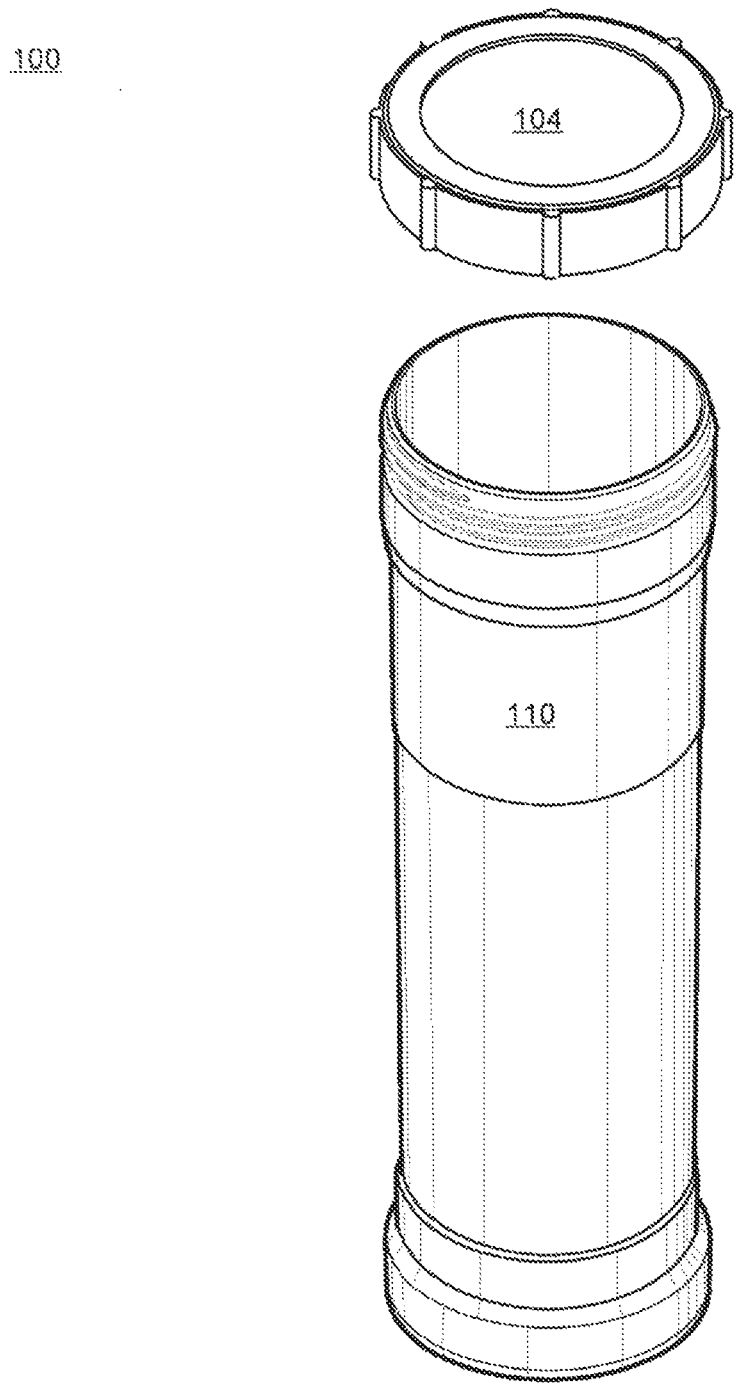
FIG. 1 shows a side view of prior art slush container 100 with slush bottle 110 with cap 104.
Figure 2:
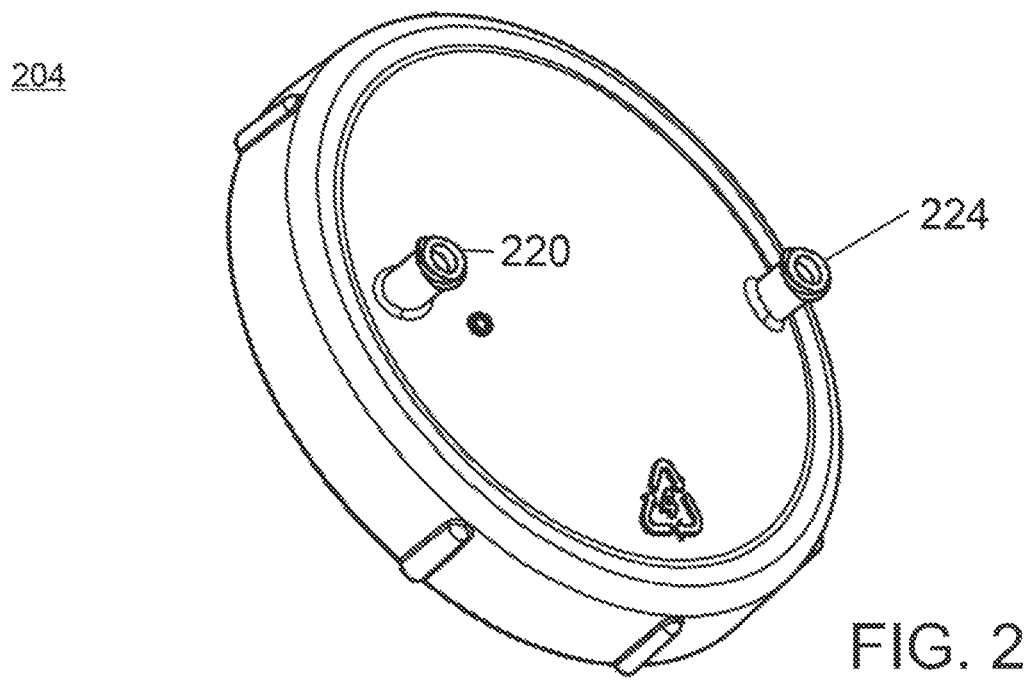
FIG. 2 and FIG. 3 show a top perspective view of cap 204 that can fit onto a slush bottle such as shown as slush bottle 110 in FIG. 1.
Figure 3:
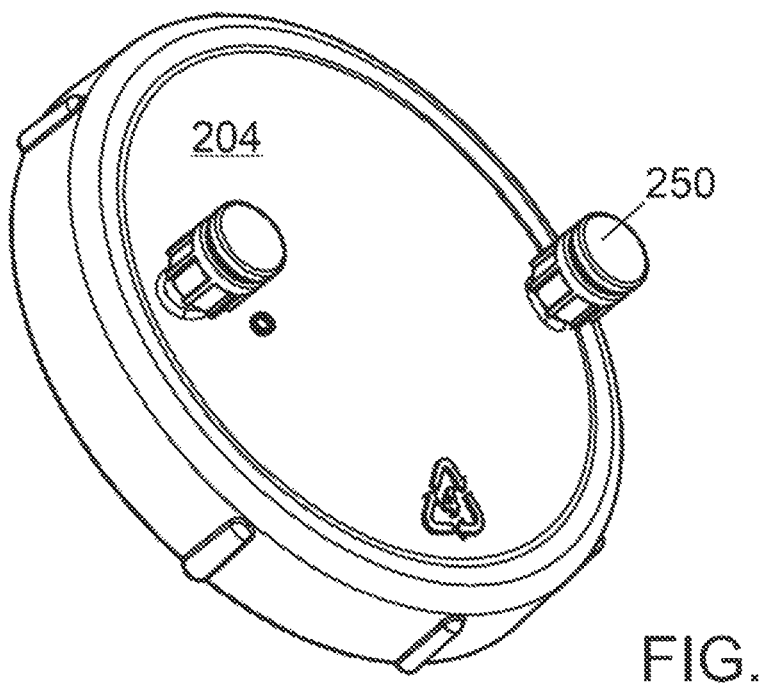

FIG. 2 and FIG. 3 show a top perspective view of cap 204 that can fit onto a slush bottle such as shown as slush bottle 110 in FIG. 1. Cap 204 has a pair of ports 220 and 224 which each provide a passageway through the cap so that liquid or gases (such as air) may pass through the cap 204 while the lid remains attached to a slush bottle.

FIG. 2 shows the cap 204 without the cap plugs 250. FIG. 3 shows the cap plugs 250 in the ports 220 and 224 to seal the ports 220 and 224. The ports 220 and 224 may start sealed and remained sealed until the slush bottle 240 with liquid to be made into sterile slush is initially sealed by the cap 204. After the slush bottle has been processed so that the slush bottle and cap 204 now encapsulate surgical slush for use in a surgical procedure, the cap plugs 250 may be removed so that slush may be provided through one of the ports 220 or 224 while using the other port as a vent to allow gas to flow into the volume defined by the slush bottle and the interior side of the cap 204 as slush leaves that volume.

Figure 4:
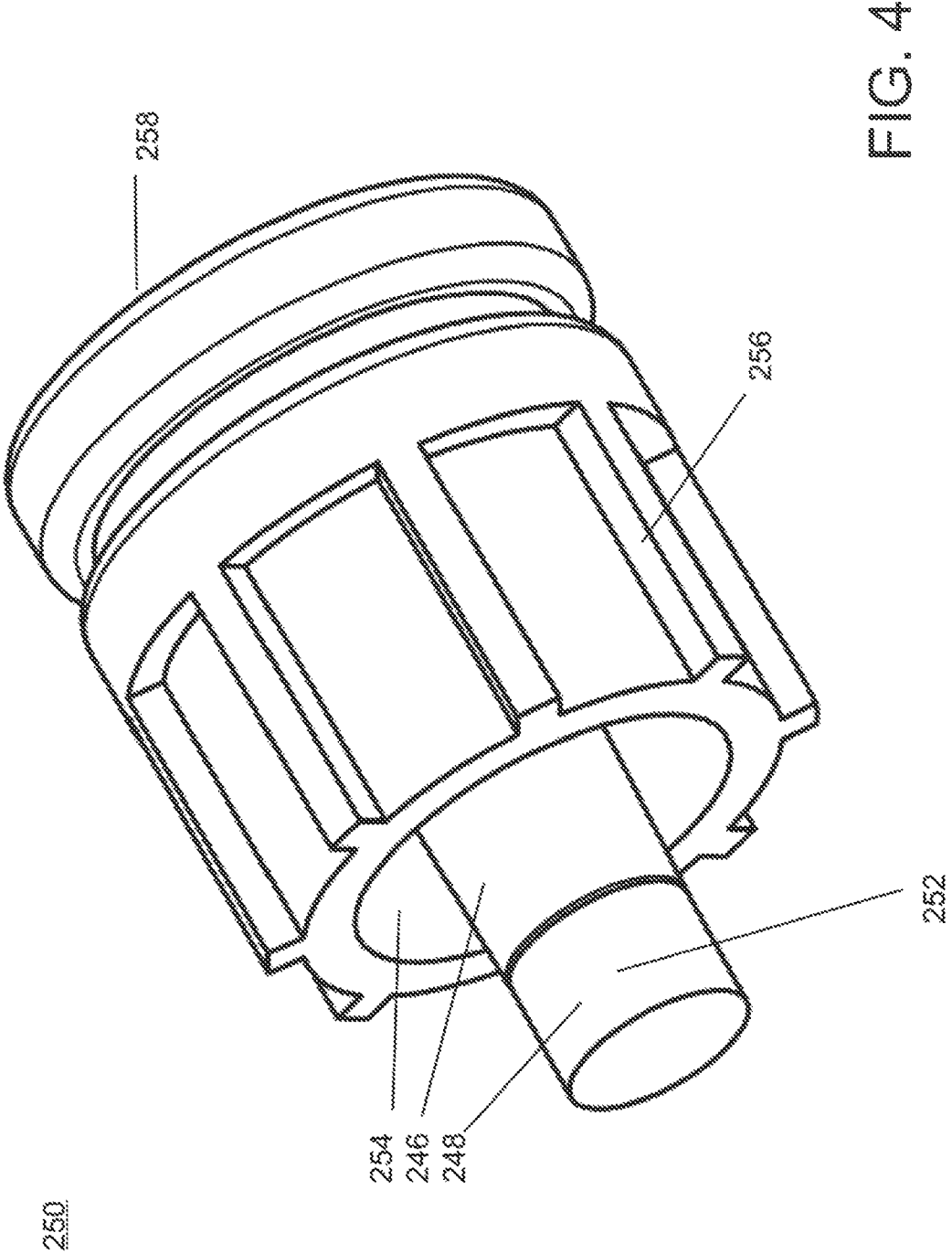
FIG. 4 shows a bottom perspective view of the cap plug 250.

FIG. 4 shows a bottom perspective view of the cap plug 250. The cap plug 250 has a stopper 252 that forms an interference fit with the interior walls of the ports 220 or 224. The stopper 252 has a tapered portion 246 that forms the interference fit and a cylindrical portion 248 that seals the inlet to the port to prevent ice from forming in the port inlet. The stopper 252 could be made of polypropylene or another suitable material. The exterior walls of the port 220 or 224 fit within annular port cavity 254. The annular port cavity could employ a Luer fitting thread or another thread type which would interact with corresponding threads on the ports. A knurled perimeter 256 facilitates a gloved end user in twisting the engaged cap plug 250 in order to remove the cap plug 250 from the port 220 or 224 when the end user wishes to obtain surgical slush for a medical procedure.

Figure 5:
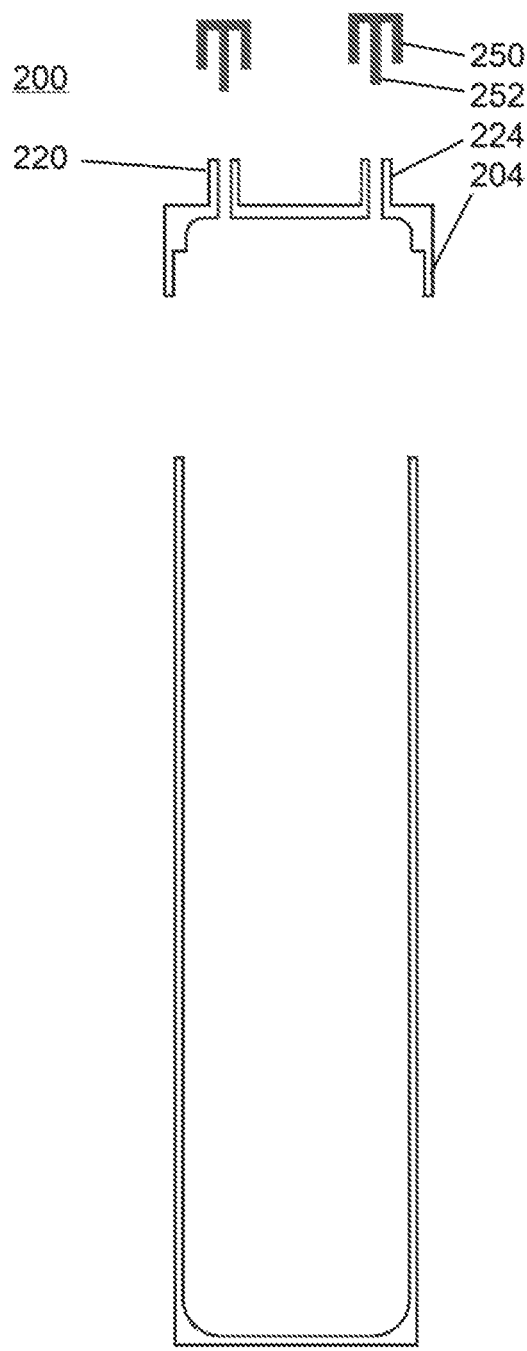
FIG. 5 shows a side view of a cross section of an exploded view of sealed slush container 200.

FIG. 5 shows a side view of a cross section of an exploded view of sealed slush container 200. Sealed slush container 200 has cap 204, cap plugs 250, and slush bottle 240. This simplified drawing does not show the threads within cap 204 that would engage with corresponding threads on the upper portion of slush bottle 240.

Figure 6:
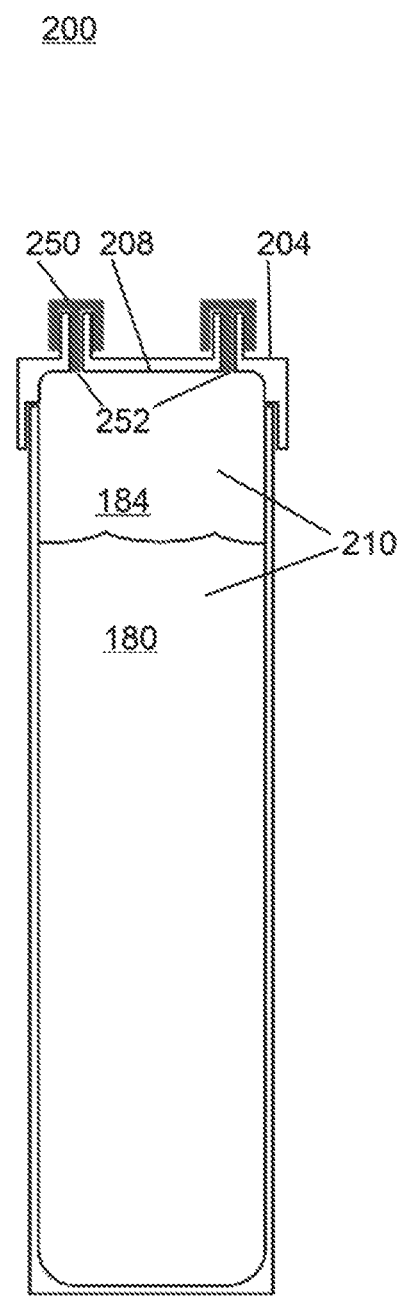
FIG. 6 shows a cross section of the sealed slush container 200.

FIG. 6 shows a cross section of the sealed slush container 200. Shown in this view are cap 204, slush bottle 240 and cap plugs 250 covering ports 220 and 224 (see FIG. 5). Slush container 200 has a liquid 180 such as sterile saline which may include additives and air 184 as the preferred processes for making sterile slush with atraumatic particles requires some air in the sealed slush container to allow for sloshing of the slush slurry to help dislodge slush from the interior 210 of the sealed slush container 200.

A careful observer will note that the distal ends of the stoppers 252 of the two cap plugs 250 extend at least to the interior wall 208 of the cap 204. The stoppers 252 may be sized relative to the interiors of the ports 220 and 224 to actually extend beyond the interior wall 208 of the cap 204 and into the interior 210 of the sealed slush container 200 so as to preclude the formation of ice within the ports 220 and 224. The sealed slush container 200 is ready to be sent to a slush making device such as described within U.S. Pat. No. 9,549,843 for the Production of Well-Mixed Surgical Slush.

After the liquid within the sealed slush container 200 has been turned into a mixture of ice and liquid with a desired ratio of solid to liquid material and with desirable atraumatic spheroids of ice of substantially uniform size, it is time to use the slush. As previously noted, this slush will have a substantially uniform consistency. Desirable surgical slush will feel soft to the touch without any hard, crystalline formations. The slush is likely to be 30 to 50% solid in order to make the material relatively easy to pump to the treatment site.

Figure 7:
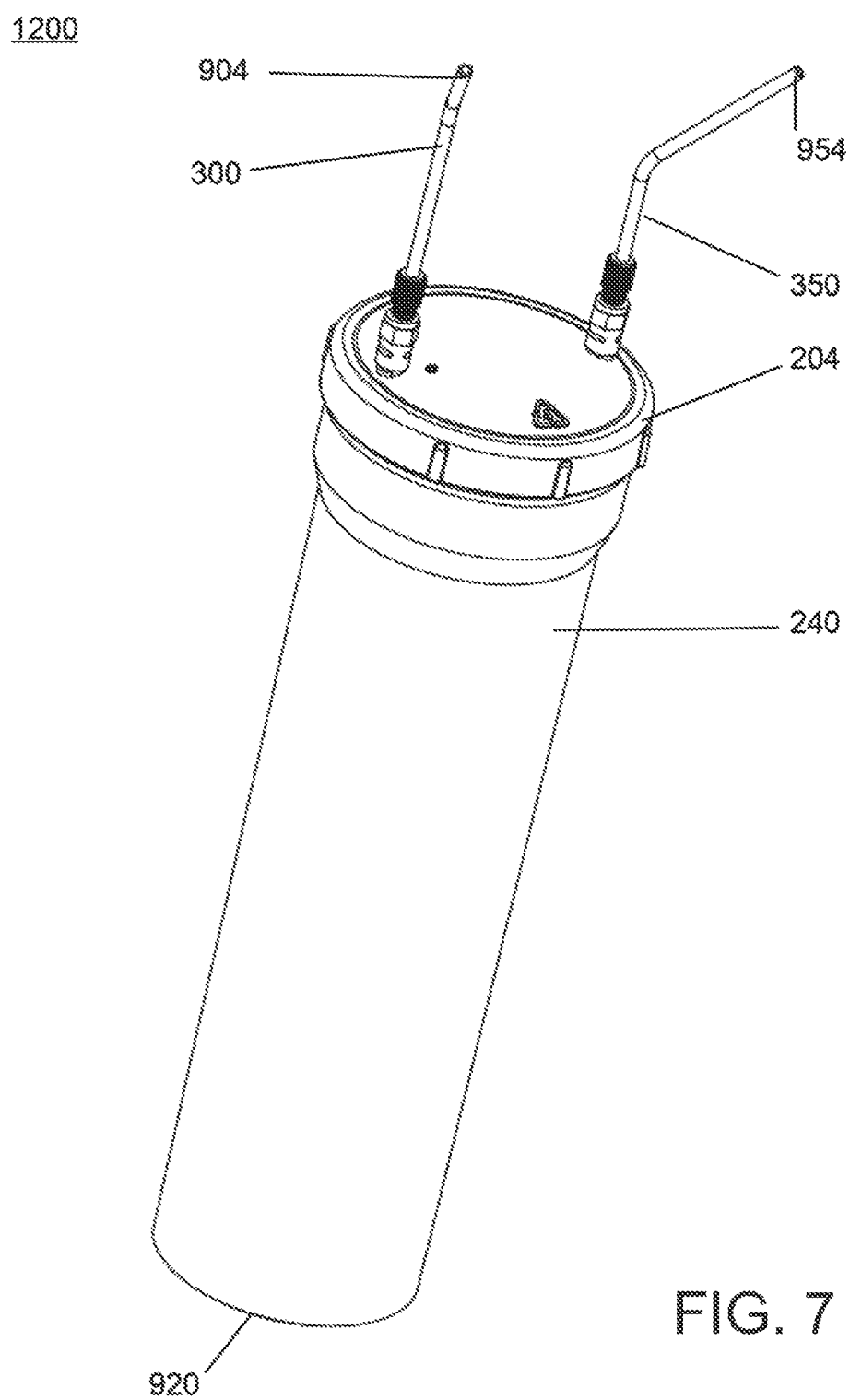
FIG. 7 shows a slush bottle 240 with an attached slush cap 204 after removal of the two cap plugs 250 and replacement with a slush output connector 300 and a vent tube 350.

FIG. 7 shows a slush bottle 240 with an attached slush cap 204 after removal of the two cap plugs 250 and replacement with a slush output connector 300 and a vent tube 350. To avoid confusion with the slush container 200 with the two cap plugs 250, this container with the slush output connector 300 and the vent tube 350 will be called the slush feed container 1200.

The slush output connector 300 can be a standard fitting to allow a long flexible tube to be connected similar to the tubing used for an IV connection. In some applications, the tubing may be run through a peristaltic or similar pump.

The vent tube 350 may include a filter if the vent tube will be used in a non-sterile environment. The vent tube 350 may include a fitting to allow a long tube (possibly flexible) to be attached to the vent tube 350 so that the end of the connected tubing is high enough that slush does not spill out of the end of that tubing during agitation of the slush feed container 1200. If a check valve is used with the vent tube 350 then the height of the end of the tubing is not important.

Another alternative is to connect the vent tube 350 to a pressurized source of air or another gas.

Figure 8:
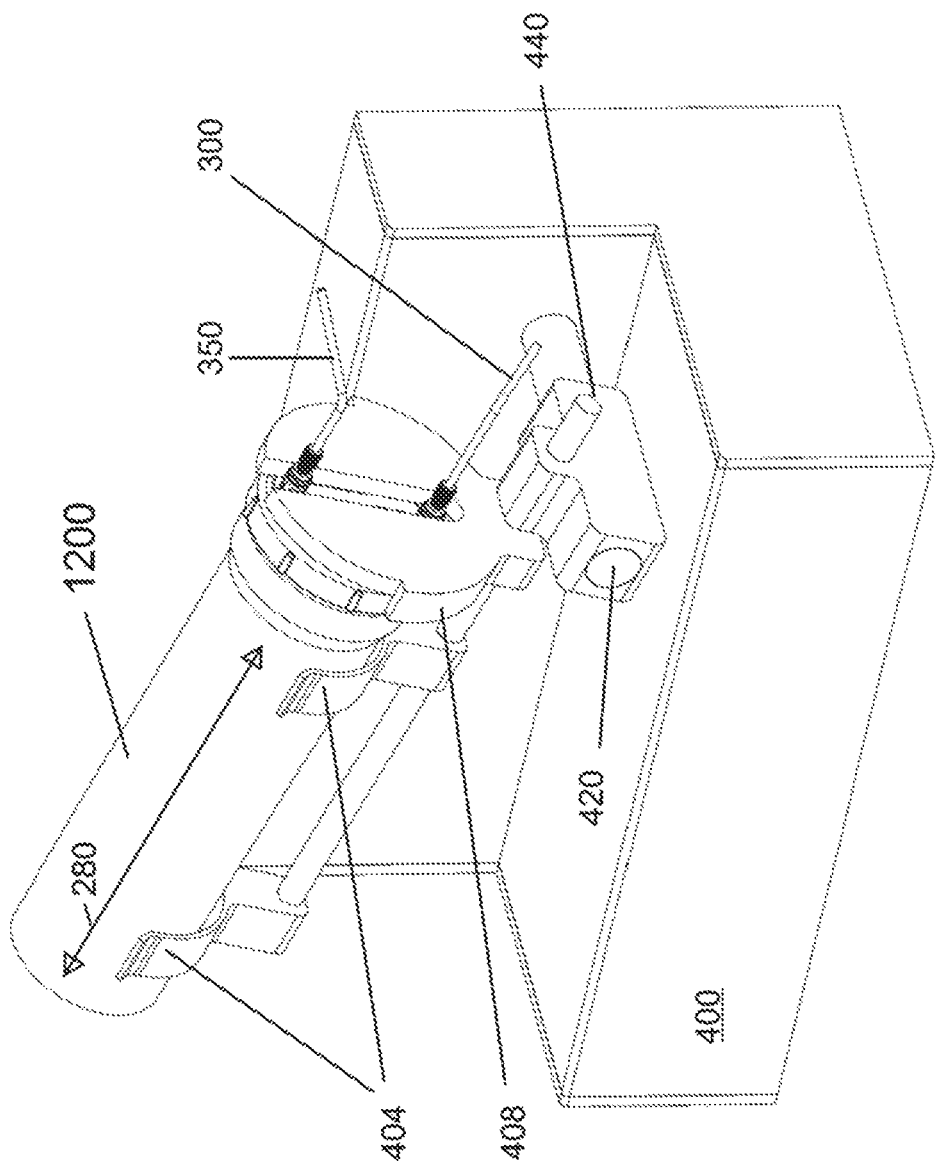
FIG. 8 shows the slush container 200 inserted into a slush mixing device 400. The slush mixing device 400 secures the slush feed container 1200 with the slush cap 204 and the slush output connector 300 located lower than the end of the slush bottle 240 that is remote from the slush cap 204.

FIG. 8 shows the slush feed container 1200 inserted into a slush mixing device 400. The slush mixing device 400 secures the slush feed container 1200 with the slush cap 204 and the slush output connector 300 located lower than the end of the slush bottle 240 that is remote from the slush cap 204. The slush mixing device 400 may limit the movement of an inserted slush feed container 1200 relative to the slush mixing device 400 with one or more supports 404 and the front plate 408 although those of skill in the art will understand that many other options exist for limiting or partially limiting the movement of a substantially cylindrical item relative to a machine that oscillates the item.

When the slush feed container 1200 is placed and retained within the slush mixing device 400, the slush output connector 300 can be connected to a slush feed pump (not shown) using conventional tubing and connectors. The slush feed pump can be any known pump used for precise delivery of viscous liquids or slurries such as a peristaltic pump (also called a roller pump). Peristaltic pumps are used in a number of medical applications such as to provide controlled delivery of fluids to an IV connection as the material being pumped stays within sterile tubing and never comes in contact with the pump. An overview of peristaltic pumps can be found at—://en.wikipedia.org/wiki/Peristaltic_pump and is incorporated herein by reference.

Slush mixing device 400 has a tilt shaft 420 that allows the longitudinal centerline 280 of the slush feed container 1200 to be tilted towards horizontal and titled to a cap-down orientation to cause waves of slush within the partially filled slush feed container 1200 to move back and forth to keep the slush from clumping or adhering to the walls of the slush feed container 1200. The motor drive to provide a range of tilt angles is not shown in this explanatory drawing as such matters are conventional to those of skill in the art.

The slush mixing device 400 may have a second operative shaft to provide a rocking of the slush feed container 1200. Rocking shaft 440 may be connected to an appropriate drive to rotate the cradle and the engaged slush feed container 1200 clockwise and counterclockwise around an axis running through the rocking shaft 440 and parallel to the longitudinal centerline 280. Having a second form of oscillation allows for more complex movement of the waves of slush within the slush feed container 1200. While not required, it may be advantageous to select the cycle of stimulus for the tilt shaft 420 to not be an even fraction or even multiple of the cycle of rotation for the rocking shaft 440 so that the combination of positions from the effects of the tilt shaft 420 and the rocking shaft 440 do not repeat on a frequent basis.

FIG. 9 shows a slush feed container 1200 and a portion of a slush mixing device 400. The current position of the rotating tilt shaft 420 places the longitudinal centerline of the slush feed container 1200 at about 15 degrees downward with respect to horizontal.

FIG. 10 shows a simplified cross section of the slush feed container 1200 at this 15-degree downward tilt. The simplified drawing does not show all the details for the slush output connector 300 or the vent tube 350. The liquid 180 has been converted into slush 188 which is a mixture of small particles of ice and liquid with higher mean salinity than the liquid 180 before the creation of slush 188. Air 184 or another gas fills the remainder of the interior of the slush feed container 1200. The slush 188 is more viscous than liquid 180 but still flows downward and sloshes within the interior of the slush feed container 1200.

One of skill in the art will appreciate the vent tube 350 may have a check valve to allow gas in but not allow slush 188 out. The vent tube 350 may be connected to a pressurized source of gas such as sterile air or a gas that will be non-reactive with the slush 188.

FIG. 11 shows a slush feed container 1200 and a portion of a slush mixing device 400. The current position of the rotating tilt shaft 420 places the longitudinal centerline of the slush feed container 1200 at about 30 degrees downward with respect to horizontal.

FIG. 12 shows a simplified cross section of the slush feed container 1200 at this 30-degree downward tilt.

Figure 13:
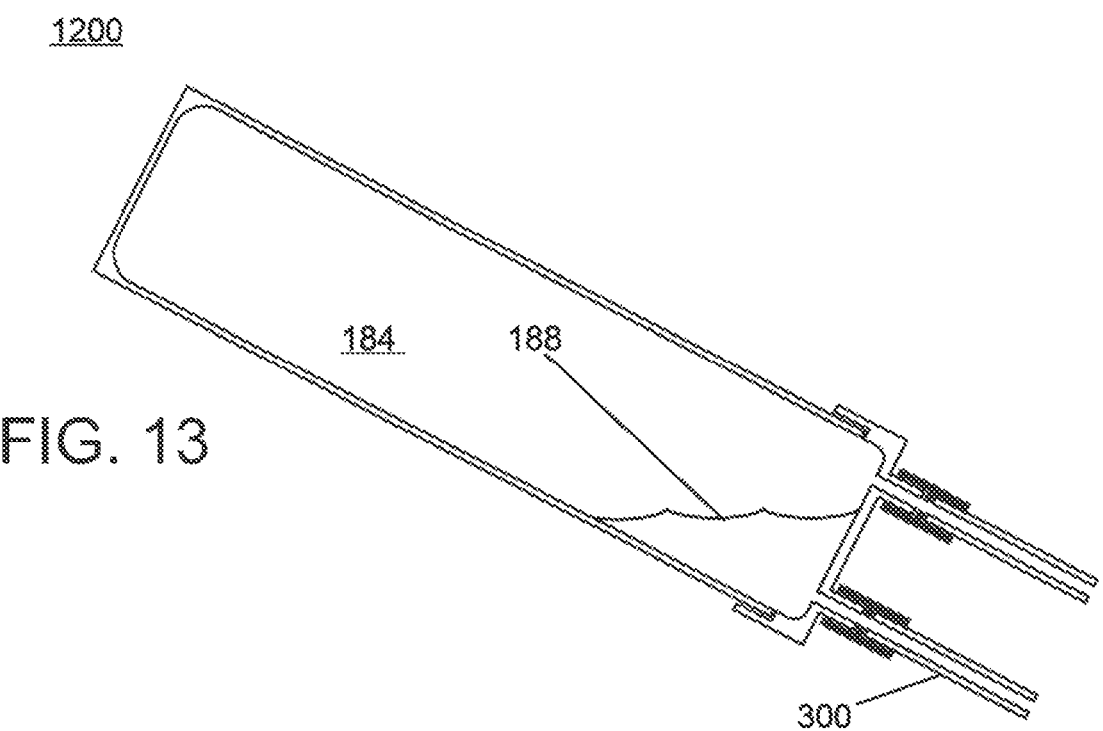
FIG. 13 shows a simplified cross section of the slush feed container 1200 at a 30 degrees downward tilt as in FIG. 12 as the quantity of slush 188 is almost gone.

FIG. 13 shows a simplified cross section of the slush feed container 1200 at a 30 degrees downward tilt as in FIG. 12 as the quantity of slush 188 is almost gone. The process would stop removing slush 188 from a slush feed container 1200 before the slush 188 stops covering the inlet to the slush output connector 300. Many pumps have counters so it will be possible to know that after a certain amount of pump operation that the slush feed container 1200 is sufficiently depleted that it is time to switch to another slush feed container 1200. Even with the variation in actual flow volume that may occur with a peristaltic pump, the degree of variability will not interfere with being able to reliably remove the slush feed container 1200 before pulling air into the outlet line.

Figure 14:
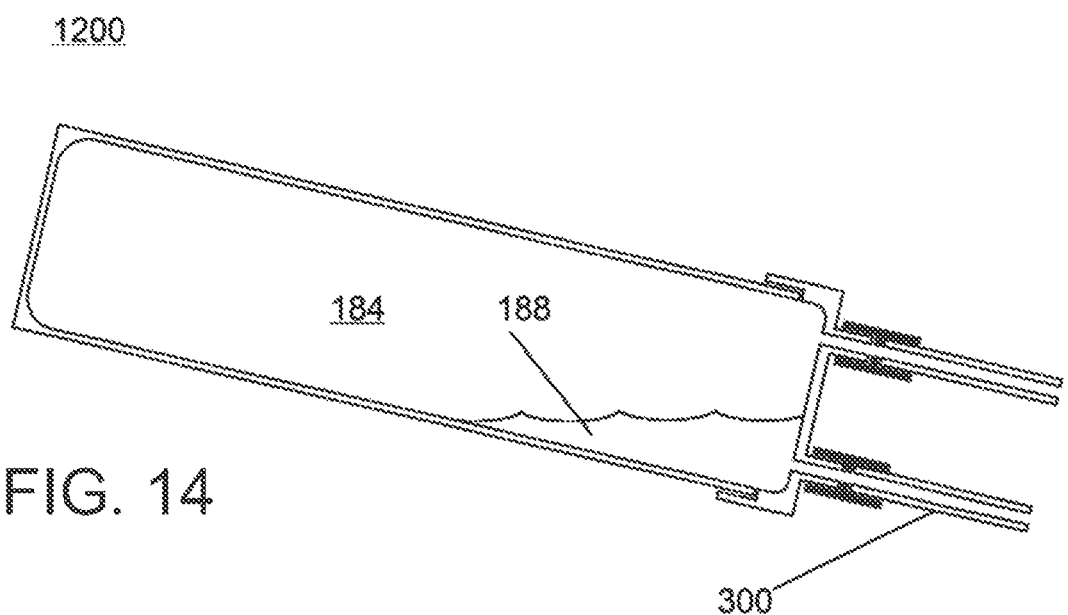
FIG. 14 shows a simplified cross section of the slush feed container 1200 at a 15 degrees downward tilt as the quantity of slush 188 is almost gone.

FIG. 14 shows a simplified cross section of the slush feed container 1200 at a 15 degrees downward tilt as the quantity of slush 188 is almost gone. Note that even with relatively little slush 188 remaining, the inlet to slush output connector 300 is covered.

Rocking.

FIG. 15 and FIG. 16 show a slush mixing device 400 that has active rocking imposed by rocking shaft 440 upon the cradled slush feed container 1200. Optionally, the supports 404 and the gap 412 in front plate 408 may be sized relative to the shape of slush feed container 1200 so that rocking of the slush feed container 1200 causes the slush feed container to continue rolling as the rocking shaft 440 reverses direction. The slush feed container 1200 can rotate far enough to hit the supports 404 which are now stopped or moving in the opposite direction. Ports 220 may make contact with the walls of the gap 412 in front plate 408 but this is not required.

The range of rocking does not need to be symmetric relative to having the gap 412 of the front plate 408 at 12 o'clock. The rocking may be in the range 15 or 20 degrees to each side.

Temperature Maintenance of the Slush Feed Container.

Figure 17:
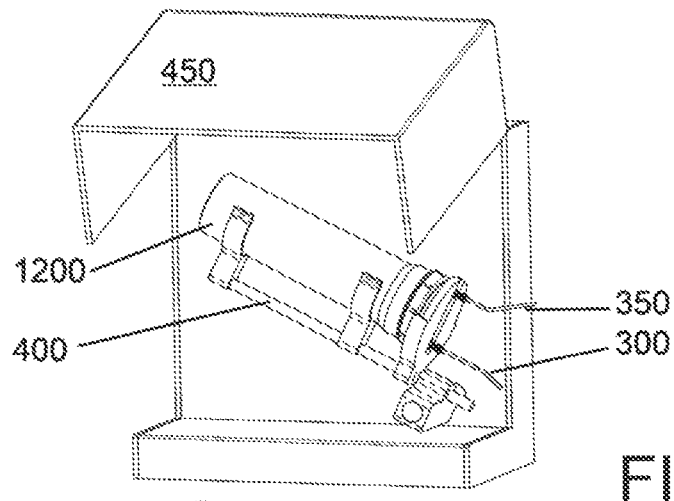
FIG. 17 shows a slush feed container 1200 in a slush mixing device 400.

FIG. 17 shows a slush feed container 1200 in a slush mixing device 400. The slush mixing device 400 may have a housing 450 which creates a finite volume of air that can be cooled using refrigeration techniques that would chill the interior of the housing 450 and the slush mixing device 400 to maintain the slush 188 with an ice/liquid mix ratio that is desired within the slush feed container 1200. As noted above, the salinity of the remaining liquid increases as the amount of ice in the slush 188 increases. This means that the temperature to freeze additional ice continues to move downward as the amount of ice increases and thus the salinity of the remaining liquid increases. Thus, careful control of the temperature will control the equilibrium ratio of ice to liquid. One of skill in the art will appreciate that the simplified drawing in FIG. 17 does not include the openings in the housing 450 that would be required for one or more tubes to pass slush out of the housing 450 from slush output connector 300.

Figure 18:
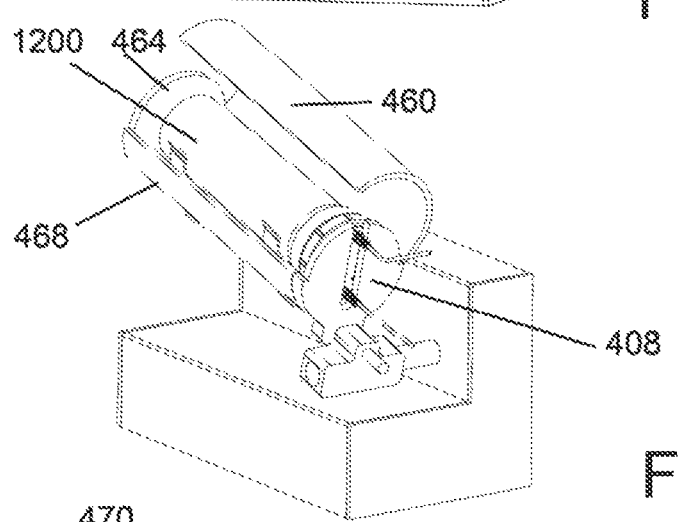
FIG. 18 illustrates another form of temperature maintenance for the slush feed container 1200.

FIG. 18 illustrates another form of temperature maintenance for the slush feed container 1200. The slush mixing device 400 still has front plate 408. The front plate 408, lower body 468, rear wall 464, and clam shell top 460 can substantially encapsulate the slush feed container 1200 with insulating materials to limit the flow of heat to the slush feed container. Use of just insulation to limit melting will mean that the ratio of ice to liquid will change as the slush feed container 1200 slowly warms. Thus, an insulation-only solution would be selected for applications where the slush is used relatively rapidly.

Figure 19:
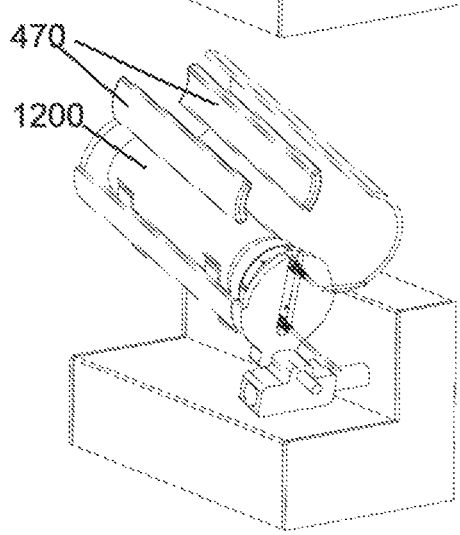
FIG. 19 is like FIG. 18 with an insulating encapsulation for the slush feed container 1200 but FIG. 19 adds one or more cooling plates 470.

FIG. 19 is like FIG. 18 with an insulating encapsulation for the slush feed container 1200 but FIG. 19 adds one or more cooling plates 470. The cooling plates 470 may be shaped to approximate the outer diameter of the slush feed container 1200. The cooling plates may be made of a material with a high thermal mass and be cooled to a temperature at or below the temperature range for the slush 188. The cooling plates 470 may be filled with a material that undergoes a phase change at a temperature selected to maintain the temperature of the slush 188 without inducing unwanted additional freezing of the slush 188. The cooling plates 470 may be replaced with other cooling plates 470 periodically to provide extended temperature maintenance of the slush 188 within the slush feed container 1200.

The cooling plates 470 may be made for aluminum. The cooling plates may be prechilled to around −10 degrees Celsius to compensate for thermal losses and to cool the internal supports in order to keep the slush 188 within a range of −4 to −5 degrees Celsius. A slush with a different target maintenance temperature may merit use of cooling plates 470 with a different initial temperature.

Process of Use.

Figure 20:
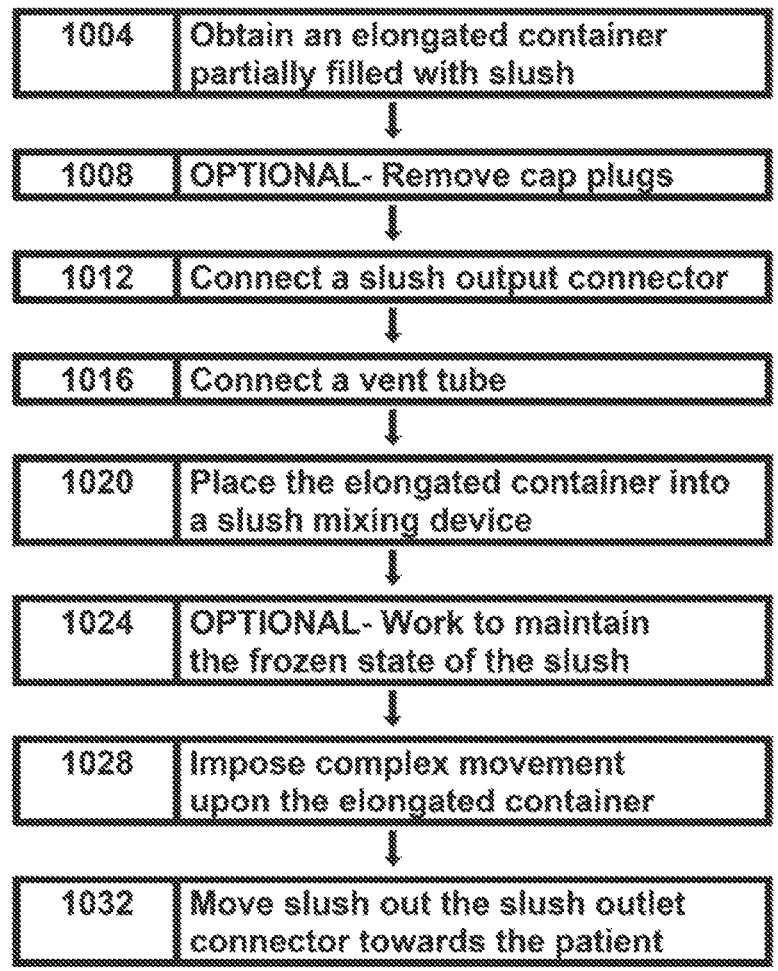
FIG. 20 contains a flowchart of process 1000 for delivery of well-mixed, atraumatic sterile slush through a tube towards a patient.

FIG. 20 contains a flowchart of process 1000 for delivery of well-mixed, atraumatic sterile slush through a tube towards a patient.

Step 1004—Obtain an elongated container partially filled with atraumatic sterile slush with a first port and a second port. The process is can use any elongated container with the relevant ports on one end. The elongated container may have a top end with ports that cannot be reversibly removed from the rest of the elongated container. The elongated container may be a slush bottle and cap as shown in the figures for this disclosure. The cap with the set of two ports may have been placed on the slush bottle before the liquid within the slush bottle was converted into slush or the cap may have replaced an initial cap that was used during the production of slush. Alternatively, the slush may have been made in a first container and then transferred to the slush bottle to partially fill the slush bottle before the cap with the set of two ports was engaged with the slush bottle.

Step 1008—Optionally the two ports may have been sealed with cap plugs that prevent movement of material through the ports and block liquid from entering from the interior of the slush bottle to the port so as to preclude the formation of ice within the ports.

Step 1012—Connect a slush output connector to one of the two ports. The slush output will ultimately be placed in fluid communication with the delivery site within the patient.

Step 1016—Connect a vent tube to the other one of the two ports. The vent tube will be used to provide a pathway for gas to enter the elongated container. The output port and the vent port may be specialized ports that are only used for one purpose or the two ports may be interchangeable.

Step 1020—Place the elongated container into a slush mixing device. Those of skill in the art will appreciate that the elongated container may be placed into the slush mixing device before or after the connections are made to the ports and the connections to the ports may be made in any order.

Step 1024—Optional Step—Work to maintain the frozen state of the slush. Depending on the length of time that this elongated container of slush will be in use, it may be helpful to retard the melting of the slush inside the capped bottle that would naturally occur when the ambient air temperature of the room is above the melting temperature for the slush. As noted elsewhere in this disclosure this effort could employ:

chilling air in a housing that encloses the elongated container and the slush mixing device;

using insulation around the elongated container to slow the heat transfer from ambient air to the slush within the elongated container;

using cooling plates that are put in contact or proximity with at least portions of the elongated container to absorb heat. This may use chilled plates of high thermal mass and may use some material that undergoes a phase change at an appropriate temperature to maintain the slush but not further freeze the ice/liquid mixture that forms the slush. For a lengthy use of a single elongated container, the cooling plates may be swapped out to provide additional cooling capacity; or using two or more of these options.

Step 1028—Use the slush mixing device to impose complex movement upon the elongated container that is partially filled with slush. This complex movement will cause movement of the slush with the elongated container to help maintain the well-mixed, atraumatic sterile slush in a state appropriate for delivery through a tube. The complex movement may include a cycle of tilting of the longitudinal centerline of the elongated container between the bottle bottom and the cap. The tilting will cause movement of slush along an axis from the bottle bottom to the cap. The complex movement may include rocking of the elongated container around a rocking axis different from the longitudinal centerline of the elongated container. To maintain a steady supply of slush, the port with the slush outlet connector will need to be maintained below horizontal so that slush is available to the port even as the supply of slush within the elongated container is near the end.

Step 1032—Move slush out the slush outlet connector towards the patient. Those of skill in the art will recognize the use of the slush mixing device to impose complex movement upon the elongated container is most likely initiated before moving slush out of the slush outlet connector but the movement of slush out of the slush outlet connector could occur first as long as the complex movement is initiated shortly thereafter.

Those of skill in the art will appreciate that delivery of material to a patient can be achieved simply by positioning the reservoir of material well above the patient so that gravity is the sole driver. Those of skill in the art will appreciate that for a material like slush to be forced through tubing to reach a delivery site within a patient, that a pressure gradient is useful.

The pressure gradient could be achieved by using a pressurized gas source that ingresses the elongated container through the vent tube and the connected port. The pressurized gas would push out slush through the port connected to the slush output connector and the subsequent flow path to the delivery site within the patient. The pressurized gas may be air but may be another gas.

Alternatively, the pressure gradient could be achieved by using one or more pumps on the path between the slush output connector or the delivery site within the patient. When using pumps, the vent tube may allow ambient air to pass through the vent tube and into the elongated container. Optionally, a filter may be used on this flow path for air entering into the elongated container. Nothing precludes using pressurized gas in combination with one or more pumps to provide the pressure gradient to move slush to the delivery site within the patient.

Material Choices.

Slush bottle 240 and cap 204 or a different elongated container may be made of highly hydrophobic materials with smooth surface finishes that work well for the teachings of the present disclosure. Thus, material choices made with or coated with Teflon® material work well in the context of this disclosure. Coatings will work well but may not be ideal choices for the slush containers that are intended to go through multiple sterilization and use cycles as any scratches or removal of coating may cause slush to adhere to the underlying material. Thus, elongated containers made of a hydrophobic material are preferred over slush containers with coated interiors.

The term Teflon materials is actually an imprecise statement. E.I. DuPont De Nemours and Company Corporation ("DuPont") owns a series of registered trademarks for various uses of material containing polymers of fluorinated hydrocarbons. There are actually several different materials that fall within this category of materials covered by the Teflon mark. The materials that fall within the category of materials covered by the Teflon mark may also be provided by other sources of goods. Thus, a focus on the chemical names rather than the trademarked product names is appropriate. Those of skill in the art will appreciate that the production of medical components often uses a medical grade supply that is created under more stringent process controls and has fewer impurities. Medical grade resin may be used here to make the elongated containers.

Polytetrafluoroethylene (PTFE) is the most commonly provided material under the Teflon trademark and is often mistakenly associated by the public as synonymous with Teflon® material. Other materials sold under the Teflon name are a class of perfluoroethers. Prominent in the perfluoroether materials is perfluoroalkoxy alkanes (PFA). —://www.guarniflon.com/index.php/en/materials/pfa.html. There are other materials in this group that have different ratios of PTFE and methylvinylether (MVE). One such material is known as MFA. —://www.guarniflon.com/index.php/en/materials/mfa.html.

PFA like PTFE is known for resistance to chemicals (chemically inert), being hydrophobic, and having extremely low coefficients of friction. One way that PFA is superior to PTFE is that PFA polymer may be melt processed which is useful when seeking to create slush containers by injection molding. Another drawback of PTFE is that it is less dimensionally stable than PFA. Dimensional stability rather than a tendency to creep is useful when a slush container is being used through multiple sterilization cycles so that a slush container lid continues to fit all the different slush containers that just underwent sterilization.

Another material in the Teflon family that may be injection molded is FEP (fluorinated ethylene propylene) which is a copolymer of hexafluoropropylene and tetrafluoroethylene. FEP differs from the PTFE (polytetrafluoroethylene) resins in that it is melt-processable using conventional injection molding and screw extrusion techniques (see —://en.wikipedia.org/wiki/Fluorinated_ethylenepropylene). This material has been tested and found to be viable for use in slush containers used in accordance with the teachings of this disclosure. PFA is preferred over FEP as PFA is harder and more dimensionally stable than FEP.

While PFA and FEP are preferred materials, acceptable results may be obtained with PET (sometimes called PETE) or with the related material PETG (PETG (Polyethylene Terephthalate Glycol-Modified). The differences between PET and PETG are summarized at —://www.plasticingenuity.com/packaging/differences-between-petg-and-apet/.

As such elongated containers made with PFA, FEP, or other suitable materials are hydrophobic and have extremely low surface friction, ice crystals tend not to form or stick to the walls of the slush container. The coefficient of friction (both static and dynamic) for various products known as Teflon including PTFE, FEP, and FPA are extremely low relative to other solid materials. The use of elongated containers made from materials that tend not to have ice crystals adhere to the walls of the elongated container promotes mixing when used in connection with an oscillating agitation.

Having a situation where ice does not form on the container wall, and mixing to keep ice from building up close to the wall more than near the longitudinal centerline of the elongated container, allows use of a slush making machine with ambient air that is chilled well below the freezing temperature range for the saline. Reducing the ambient air temperature increases the rate of cooling of the container contents which is desirable when done without the adverse consequences of creating unacceptable ice deposits on or near the walls of the slush bottle 240 or cap 204.

The material choice for the elongated container may allow sterilization of the container per standard hospital protocols. Those of skill in the art recognize that there are a number of different protocols and some may be contraindicated for certain materials. Examples of common sterilization protocols include using EtO (ethylene oxide), autoclave, and low temperature plasma. Other methods are known to those of skill in the art.

Alternatives and Variations

Tilt Angle Ranges

A range of tilt angles of 15 to 30 degrees was used for the figures in this specification. The minimum tilt angle may be different than 15 degrees of declination. Those of skill in the art will recognize that having a minimum tilt angle less than 15 degrees may impact the fraction of slush that is not used with each slush feed container 1200.

For example, a minimum tilt angle of 15 degrees with a particular level of agitation of the slush feed container may lead to leaving about 150 ml of slush 188 in a slush feed container 1200 that was initially filled with one liter of sterile saline. Likewise, the use of a minimum tilt angle less than 15 degrees may require a reduction in the intensity of the tilt angle changes and rocking so that wave troughs do not introduce air into the inlet of the slush output connector 300. Conversely, air detection or air mitigation mechanisms between the slush feed container 1200 and the patient may allow for a minimum tilt angle of less than 15 degrees as undesirable results from air entering the inlet are not a problem.

Likewise, the maximum tilt angle of 30 degrees may be modified to be less than 30 degrees or more than 30 degrees. Those of skill in the art will appreciate that the tilt shaft 420 does not have be separated from the slush feed container 1200 by the front plate 408. The tilt shaft 420 could be located under the slush feed container 1200 perhaps midway along the length of the slush feed container 1200.

More than Saline.

While the discussion above focused on surgical slush made from sterile saline, the teachings of the present disclosure could be applied to the creation of surgical slush that is made of a mixture of medical saline or sterile water and clinically appropriate materials. The clinically appropriate materials may include sugars, vitamins, enzymes, or other bioactive agents. Glycerol may be added to the slush. The operation of the slush freezer to make the slush and the slush cradle to maintain the slush 188 may need to be adopted for a particular use such as altering the temperature settings of the expected amount of time to create the slush, but these adjustments can be made by those of skill in the art.

The present disclosure does not require standard 0.9% saline to be a base material for use in creating the slush for injection.

Non-circular Cross Section.

While the cross section of the slush bottle 240 has been indicated as substantially cylindrical, other shapes are possible for the slush bottle or the elongated container generally, including an oval or an extremely rounded tri-lobe or square shape. The shape should avoid the use of sharp corners which might retain slush. Use of shapes other than circular may require adjustments to the rate of cooling or the agitation levels in order to compensate for any tendency of slush to form in the highly rounded corners. Thus the present disclosure encompasses implantations with a cross section of the elongated container taken perpendicular to a longitudinal centerline of the elongated container from bottom to port end where the cross section is not a circle.

Single Use Slush Containers.

While the disclosure teaches the use of slush bottles and lids that may undergo sterilization and reuse, the teachings of this disclosure do not require re-use. Single-use slush containers may be used, particularly for one piece elongated containers with an integrated top with ports. The single-use slush containers may come prefilled with an appropriate volume of liquid such as sterile saline.

The single-use containers may come initially with a simple cap 104 (FIG. 1) which is replaced with a cap 204 having a pair of ports 220 and 224 for use in creating a slush feed container 1200. The single-use containers may be an elongated container with integrated ports wherein the elongated container is already partially filled with the liquid to become slush or the elongated container may be partially filled with liquid through one or more ports after receipt.

Speed of Agitation.

The speeds of tilting and rocking will be selected to ensure adequate mixing of the slush 188 while avoiding wave movements that are sufficient to capture large bubbles after waves make contact with an interior wall of the elongated container.

Ports May be Specialized.

This disclosure showed two interchangeable ports 220. Interchangeable ports are not a requirement of this disclosure and it may be desirable to have one port that is intended for use with the slush output connector 300 and a different port that is intended for use with the vent tube 350. For example, the internal diameter of the interior of the port used for the vent tube 350 may be smaller than the internal diameter of the interior of the port used with the slush output connector 300 or the two ports may use different fitting connectors.

Instrumentation and Controls.

Bubble detectors may be placed between the slush feed container 1200 and the pump to at minimum provide an alarm if a discernable bubble is present in the line. A clinician may stop the delivery of slush when an alarm is given by using the controls for the device for delivery of slush to the patient. Bubble detectors may be linked with the control system to stop the pump pending intervention by the clinician to indicate that the problem has been cleared.

A pressure sensor may be placed to detect pressures in the outlet from the pump to the device delivering slush to the patient. This pressure sensor would respond in the event that a blockage was limiting the delivery of slush but the peristaltic pump or other pump was continuing to operate.

Alternatives to Use of a Pump.

An alternative to the use of a pump connected to the slush output connector 300 is to apply pneumatic pressure to the interior of the slush feed container 1200 through the vent tube 350. Applying pneumatic pressure to the interior of the slush feed container 1200 would force slush 188 out of the slush output connector 300 without reliance on a pump. Pneumatic feed systems are commonly used in delivery of paint, gasoline, and wine.

Thus, the term "delivery mechanism" should be interpreted broadly enough to include pumps operating on slurry material coming from the slush feed container 1200 but also systems to apply controlled amounts of pneumatic pressure to the interior of the slush feed container 1200.

Those of skill in the art will recognize that the application of force to impose a pressure gradient across the elongated container to force slush out of a port towards the patient may be applied intermittently as the delivery of slush to the patient may not be continuous. Alternatively, the application of force may be constant but a control used by the medical professional may close a flow path to the patient near the point of delivery for the slush.

Cap with Integrated Components.

This disclosure describes a cap 204 with two ports 220 and 224 that are subsequently connected to a slush output connector 300 and to a vent tube 350 as shown in FIG. 7. This works well with a process that partially fills a slush bottle with saline and then places a cap 204 with the ports sealed with port plugs 250 into a slush making machine before bringing the slush feed container 1200 now partially filled with slush for use. Not having the slush output connector 300 and the vent tube 350 protruding during the agitation in the slush making machine such as described in U.S. Pat. No. 9,549,843 for the Production of Well-Mixed Surgical Slush is sensible.

One of skill in the art will appreciate that if the slush making machine was provided a partially filled slush bottle sealed with a simple cap 104 (FIG. 1) that a slush delivery cap with integrated slush output connector 300 and integrated vent tube 350 preconnected to channels through the delivery cap could provide a viable route to a status equivalent to FIG. 7. This would be an alternative route to an elongated container with a fluid communication path from a proximal tip of the slush output connector to the interior of the elongated container and a fluid communication path from the proximal tip of the vent tube to the interior of the elongated container. Such a elongated container would be suitable for use in the slush mixing device of FIG. 8 and in the rest of the process.

Periodic Cessation of Repetitive Movements.

This disclosure teaches the use of one or more types of repetitive movements in order to agitate the slush through varying types of movement within the partially filled elongated container. The repetitive motion may be maintained without interruption from soon after the elongated container is placed in the slush mixing device until the elongated container is no longer able to provide slush or the need for slush has ended. One of skill in the art will appreciate that the repetitive movement may be stopped for a short period of time without adverse impact. The cessation of movement could be one type of movement or all movement. The cessation of movement could be a routine part of the cycle of movement. For example, the movement may proceed for 45 seconds and then cease for 15 seconds before repeating the cycle.

One of skill in the art will recognize that some of the alternative implementations set forth above are not universally mutually exclusive and that in some cases additional implementations can be created that employ aspects of two or more of the variations described above. Likewise, the present disclosure is not limited to the specific examples or particular embodiments provided to promote understanding of the various teachings of the present disclosure.

Where methods and/or events described above indicate certain events and/or procedures occurring in a certain order, the ordering of certain events and/or procedures may be modified. Additionally, certain events and/or procedures may be performed concurrently in parallel processes, when possible, as well as performed sequentially as described above.

The legal limitations of the scope of the claimed invention are set forth in the claims that follow and extend to cover their legal equivalents. Those unfamiliar with the legal tests for equivalency should consult a person registered to practice before the patent authority which granted this patent such as the United States Patent and Trademark Office or its counterpart.

What is claimed is:

1. An assembly for use to provide slush for injection into a patient, the assembly comprising:
    a slush bottle with an interior defined by a bottle bottom at a distal end of the slush bottle, a set of at least one bottle sidewall connecting the bottle bottom to an open end of the slush bottle at a proximal end of the slush bottle;
    a cap adapted to reversibly engage with the proximal end of the slush bottle to cover the open end and form a capped bottle;
    a set of two ports that each provide one open channel from a proximal side of the cap to a distal side of the cap to allow matter to traverse through the cap while the cap is engaged with the proximal end of the slush bottle;
    a slush output connector connected an output port which is one of the set of two ports, the slush output connector having a delivery channel for delivery of slush from the interior of the capped bottle through the one of the set of two ports and the slush output connector to tubing that carries slush towards an entry point in the patient; and
    a vent tube connected to a vent port which is one of the set of two ports but not a port connected to the slush output connector, the vent tube having a vent channel that allows gas to flow through the vent tube and the vent port to allow gas to enter the capped bottle; and
    a slush mixing device that supports the capped bottle and tilts the capped bottle so that a longitudinal centerline of the capped bottle from bottle bottom to cap has a movement towards horizontal followed by movement to a second position with the cap of the capped bottle lower than the bottle bottom of the capped bottle so that a water line between the slush and a gas filled space moves within the capped bottle.

2. The assembly for use to provide slush of claim 1 wherein the vent tube is open to ambient air so that ambient air enters the capped bottle through the vent tube.

3. The assembly for use to provide slush of claim 2 wherein the vent tube includes a filter so that ambient air passes through a filter before entering the capped bottle.

4. The assembly for use to provide slush of claim 1 wherein the vent tube has a check valve so that matter from the interior of the capped bottle is precluded from movement from the interior of the capped bottle out the proximal end of the vent tube.

5. The assembly for use to provide slush of claim 1 wherein the vent tube is connected to a pressurized source of gas.

6. The assembly for use to provide slush of claim 5 wherein the pressurized source of gas is not air.

7. The assembly for use to provide slush of claim 1 wherein
    each one of the set of two ports on the cap may be connected to the slush output connector while not connected to the vent tube; and
    each one of the set of two ports on the cap may be connected to the vent tube while not connected to the slush output connector.

8. The assembly for use to provide slush of claim 1 wherein the tubing that carries slush towards the entry point in the patient is connected to a slush feed pump.

9. The assembly for use to provide slush of claim 1 wherein the slush mixing device stops the movement towards horizontal when the longitudinal centerline of the capped bottle from bottle bottom to cap is not less than 15 degrees from horizontal with the cap remaining below the bottle bottom.

10. The assembly for use to provide slush of claim 9 wherein the slush mixing device cycles the longitudinal centerline of the capped bottle from bottle bottom to cap from having the cap near 15 degrees below the bottle bottom to having the cap near 30 degrees below the bottle bottom.

11. The assembly for use to provide slush of claim 1 wherein the slush mixing device rocks the capped bottle clockwise and counterclockwise around a rocking axis running parallel to the longitudinal centerline so that rocking of the capped bottle augments the tilting of the capped bottle to agitate the slush contained in the capped bottle.

12. The assembly for use to provide slush of claim 1 wherein the slush mixing device rocks the capped bottle using a rocking cycle of a first duration and the slush mixing device tilts the capped bottle using a tilt cycle of a second duration that is different from the first duration.

13. The assembly for use to provide slush of claim 1 wherein the slush mixing device rocks the capped bottle using a rocking cycle having a range of about 40 degrees of travel.

14. The assembly for use to provide slush of claim 1 wherein the slush mixing device has a second form of oscillation of the capped bottle to impose complex movement of the slush within the capped bottle.

15. The assembly for use to provide slush of claim 1 wherein the slush mixing device and the capped bottle are in a housing so that air surrounding adjacent to at least a portion of the capped bottle is cooled to below ambient air temperature outside of the housing.

16. The assembly for use to provide slush of claim 1 wherein the capped bottle is substantially surrounded by insulative material to limit a transfer of heat from air near the capped bottle to the slush within the capped bottle.

17. The assembly for use to provide slush of claim 1 wherein the capped bottle is at least partially surrounded by at least one cooling plate which removes heat from the capped bottle.

18. The assembly for use to provide slush of claim 17 wherein at least one cooling plate includes a material that undergoes a phase change while in contact with the capped bottle that contains slush.

19. The assembly for use to provide slush of claim 1 wherein the slush bottle and the cap are both made of a hydrophobic material.

20. The assembly for use to provide slush of claim 1 wherein the slush bottle and the cap are both made of a material suitable for multiple cycles of sterilization using at least one standard hospital protocol.

21. The assembly for use to provide slush of claim 1 wherein a cross section of the slush bottle taken perpendicular to a longitudinal centerline of the capped bottle from bottle bottom to cap is not a circle.

22. The assembly for use to provide slush of claim 1 further comprising cap plugs to cover proximal ends of the set of two ports to preclude matter from traversing the cap until such movement is desired.

23. The assembly for use to provide slush of claim 22 wherein at least one cap plug engages one of the set of two ports using a threaded connection.

24. The assembly for use to provide slush of claim 22 wherein at least one cap plug engages one of the set of two ports using a stopper that forms an interference fit.

25. The assembly for use to provide slush of claim 22 wherein the cap plugs block liquids from moving from the distal side of the cap into each open channel from the proximal side of the cap to the distal side of the cap so as to preclude formation of ice within the set of two ports.

26. An assembly for use in providing slush for injection into a patient, the assembly comprising:
an elongated container with an interior defined by a container bottom at a distal end of the elongated container, a port end opposite the container bottom, and a set of at least one container sidewall connecting the container bottom to the port end at a proximal end of the elongated container;
a set of two ports that each provide one open channel from a proximal side of the port end of the elongated container to a distal side of the port end of the elongated container to allow matter to traverse through the port end of the elongated container;
a slush output connector connected an output port which is one of the set of two ports, the slush output connector having a delivery channel for delivery of slush from the interior of the elongated container through the one of the set of two ports and the slush output connector to tubing that carries slush towards an entry point in the patient;
a vent tube connected to a vent port which is one of the set of two ports but not a port connected to the slush output connector, the vent tube having a vent channel that allows gas to flow through the vent tube and the vent port to allow gas to enter the elongated container; and
a slush mixing device that supports the elongated container and tilts the elongated container so that a longitudinal centerline of the elongated container from container bottom to the port end of the elongated container has a movement towards horizontal followed by movement to a second position with the port end of the elongated container lower than the container bottom of the elongated container so that a water line between the slush and a gas filled space moves within the elongated container.

27. The assembly for use in providing slush of claim 26 wherein the slush mixing device stops the movement towards horizontal when the longitudinal centerline of the elongated container from container bottom to port end is not less than 15 degrees from horizontal with the port end remaining below the container bottom.

28. The assembly for use in providing slush of claim 26 wherein the slush mixing device cycles the longitudinal centerline of the elongated container from container bottom to port end from having the port end near 15 degrees below the container bottom to having the port end near 30 degrees below the container bottom.

29. The assembly for use in providing slush of claim 26 wherein the slush mixing device rocks the elongated container clockwise and counterclockwise around a rocking axis running parallel to the longitudinal centerline so that rocking of the elongated container augments the tilting of the elongated container to agitate the slush contained in the elongated container.

30. The assembly for use in providing slush of claim 26 wherein the slush mixing device rocks the elongated container using a rocking cycle having a range of about 40 degrees of travel.

31. The assembly for use in providing slush of claim 26 wherein the slush mixing device has a second form of oscillation of the elongated container to impose complex movement of the slush within the elongated container.

32. The assembly for use in providing slush of claim 26 wherein the slush mixing device and the elongated container are in a housing so that air surrounding adjacent to at least a portion of the elongated container is cooled to below ambient air temperature outside of the housing.

33. The assembly for use in providing slush of claim 26 wherein the elongated container is substantially surrounded by insulative material to limit a transfer of heat from air near the elongated container to the slush within the elongated container.

34. The assembly for use in providing slush of claim 26 wherein the elongated container is at least partially surrounded by at least one cooling plate which removes heat from the elongated container.

35. The assembly for use in providing slush of claim 34 wherein at least one cooling plate includes a material that undergoes a phase change while in contact with the elongated container that contains slush.

* * * * *